(12) United States Patent
Blaszczak et al.

(10) Patent No.: US 7,173,107 B2
(45) Date of Patent: Feb. 6, 2007

(54) GLYCOPEPTIDE AND PREPARATION THEREOF

(75) Inventors: Larry Chris Blaszczak, Indianapolis, IN (US); Elizabeth Anne Dingess-Hammond, Indianapolis, IN (US); William Joseph Hornback, Fishers, IN (US); Michael Scott VanNieuwenhze, Carlsbad, CA (US)

(73) Assignee: Eli Lilly and Company, Indianapolis, IN (US)

( * ) Notice: Subject to any disclaimer, the term of this patent is extended or adjusted under 35 U.S.C. 154(b) by 581 days.

(21) Appl. No.: 10/240,944

(22) PCT Filed: Apr. 18, 2001

(86) PCT No.: PCT/US01/12630

§ 371 (c)(1),
(2), (4) Date: Oct. 3, 2002

(87) PCT Pub. No.: WO01/79267

PCT Pub. Date: Oct. 25, 2001

(65) Prior Publication Data

US 2003/0187186 A1    Oct. 2, 2003

Related U.S. Application Data

(60) Provisional application No. 60/255,829, filed on Dec. 15, 2000, provisional application No. 60/197,237, filed on Apr. 18, 2000.

(51) Int. Cl.
*A61K 38/14* (2006.01)
*A61K 38/00* (2006.01)
*C07K 9/00* (2006.01)
*G01N 33/00* (2006.01)
*A01N 37/18* (2006.01)

(52) U.S. Cl. .............................. 530/322; 436/87; 514/2

(58) Field of Classification Search ................. 530/322
See application file for complete search history.

(56) References Cited

U.S. PATENT DOCUMENTS

| 4,391,800 | A | * | 7/1983 | Durette et al. ................ 514/18 |
| 4,395,399 | A |   | 7/1983 | Ovchinnikov et al. |
| 5,506,204 | A |   | 4/1996 | Aston |
| 6,008,333 | A | * | 12/1999 | Vosika et al. .............. 536/17.4 |

OTHER PUBLICATIONS

Online-Medical Dictionary. "Analogue". http://cancerweb.ncl.ac.uk/cgi-bin/omd?analogue. Jan. 10, 1998.*
Online-Medical Dictionary. "Amino acid". http://cancerweb.ncl.ac.uk/cgi-bin/omd?query=amino+acid. Nov. 13, 1997.*
Ledvina et al. (Carb. Research, 1994, 251(3), pp. 269-284; also cited in Applicant's PCT/US01/12630 Form PCT/ISA/210).*

Kantoci et al. A convenient synthetic route to the disaccharide repeating-unit of peptidoglycan. Carbohydr Res. May 1, 1987;162(2):227-35; also cited in Applicant's PCT/US01/12630 Form PCT/ISA/210.*
C. Merser, et al., "Synthesis of the Repeating Disaccharide Unit of the Glycan Moiety of the Bacterial Cell Wall Peptidoglycan"*Tetrahedron Lett.*, No. 13, pp. 1029-1032 (1973).
P. L. Durette, et al., "Synthesis of O- (2-acetamido-2-deoxy-β-D-glucosyl)—(1→4) -N-acetylmuramoyl-L-alanyl-D-isoglutamine, the repeating disaccharide-dipeptide unit of the bacterial cell-wall peptidoglycan", *Carbohydr. Res.*, vol. 77 pp. C1-C4 (1979).
S. Kusumoto, et al., "Chemical Synthesis and Biological Activities of Two Disaccharide Dipeptides Corresponding to the Repeating Units of Bacterial Peptidoglycan", *Bull. Chem. Soc. Japn.*, vol. 59, pp. 1411-1417 (1986).
S. Kusumoto, et al., "Synthesis of β(1-4)—Linked Disaccharides of *N*-Acetylglucosamine and N-Acetylmuramic Acid by Their Direct Condensation" *Bull. Chem. Soc. Jpn.*, vol. 59, pp. 1419-1423 (1986).
J. Farkas, et al., "The Synthesis of *O*- (2-Acetamido-2-Deoxy-β-D-Glucopyranosyl)—(1→4)—N-Acetylnormuramoyl-L-α-Aminobutanoyl-D-Isoglutamine", *Carbohydr. Res.*, vol. 163, pp. 63-72 (1987).
W. Kinzy, et al., "Muraminsaure als Glycosyldonor and -akzeptor", *Liebigs Ann. Chem.*, pp. 407-415 (1987).
A. Termin, et al., "6-*O*-Benzylierte Muraminsaure als Glycosylakzeptor—Synthese des GlcNAc-β (1-→4)—MurNAc-Disaccharids", *Liebigs Ann. Chem.*, pp. 789-795 (1989).
M. Ledvina, et al., "An Alternative Synthesis of O- (2-Acetamido-2-Deoxy-β-D-Glucopyranosyl)—(1→4)—N-Acetylnormuramoyl—L-α-Aminobutanoyl-D-Isoglutamine", *Collect Czech. Chem. Commun.*, vol. 54, pp. 2784-2794 (1989).
A. Termin, et al., "Synthesis of the GlcNAcβ(1-→4) MurNAcβ(1-→4) GlcNAcβ(1-→4) MurNAc Tetrasaccharide of Bacterial Peptidoglycan", *Liebigs Ann. Chem.*, pp. 527-533 (1992).
P. H. Gross, et al., "Stereochemically Pure Derivatives of Muramic and Isomuramic Acids", *Justus Liebigs Ann. Chem*, pp. 37-45 (1986).
M. P. DeNinno, et al., "A Method for the Selective Reduction of Carbohydrate 4, 6-*O*-Benzylidene Acetals", *Tetrahedron Lett.*, vol. 36, pp. 669-672 (1995).
M. Imoto, "Total Synthesis of *Escherichia coli* Lipid A, the Endotoxically Active Principle of Cell-Surface Lipopolysaccharide", *Bull. Chem. Soc. Jpn.*, vol. 60, pp. 2205-2214 (1987).
A. M. Palache, et al., "Adjuvancy and reactogenicity of *N*-acetylglucosaminyl-*N*-acetylmuramyl-dipeptide (GMDP) orally administered just prior to trivalent influenza subunit vaccine. A double-blind placebo-controlled study in nursing home residents", *Vaccine*, vol. 14, pp. 1327-1330 (1996).

(Continued)

*Primary Examiner*—Cecilia Tsang
*Assistant Examiner*—Maury Audet
(74) *Attorney, Agent, or Firm*—John A. Cleveland, Jr.

(57) ABSTRACT

The stereospecific synthesis of a glycopeptide using a triply orthogonal protection scheme is described, in particular, the synthesis of N-acetylglucosaminyl-β-[1,4]-N-acetylmuramylmonopeptide and derivatives thereof. The glycopeptide is useful for the preparation of GMDP and related compounds having a glucosaminyl-β-[1,4]-N-acetylmuramic acid disaccharide core.

46 Claims, No Drawings

OTHER PUBLICATIONS

R. M. Khaitov, et al., "Immunotherapy of Infectious Postoperative Complications with Glucosaminyl Dipeptide", *Immunotherapy of Infections Ed.*, pp. 205-211 (1994).

S. Kusumoto, et al., "Synthesis of N-Acetyl-β-D-Glucosaminyl—(1-4)—N-Acetylmuramyl-L-Alanyl-D-Isoglutamine", *Tetrahedron Lett.*, No. 45, pp. 4407-4410 (1978).

Whitesides, et al., "Synthesis of Glycosyl Phosphates Using the Fraser-Reid Activation", *J. Org. Chem.*, vol. 56, pp. 4547-4549 (1991).

Sabesan, et al., "Synthesis of glycosyl phosphates and azides", *Carbohydr. Res.*, vol. 223, pp. 169-185 (1992).

V.T. Ivanov, et al., *Immunologiya* No. 2, pp. 4-6 (1996).

I.E. Adrianova, et al., *Radiobiologiia*, vol. 32, pp. 566-570 (1992).

S.A. Hitchcock, et al, "The First Total Synthesis of Bacterial Cell Wall Precursor UDP-N-Acetylmuramyl-Pentapeptide (Park Nucleotide)", *J. Am. Chem. Soc.*, 120, pp. 1916-1917 (1998).

M. Ledvina, et al., "Synthesis of O-2-acetamido-2-deoxy-6-O-stearoyl-and -6-O- (2-tetradecylhexadecanoyl) -beta-D-glucopyranosyl-(1?4)-N-acetylnormuramoyl-L-alpha-aminobutanoyl-D-isoglutamine, lipophilic disaccharide analogues of MDP", *Carbohydrate Research*, 251, pp. 269-284 (1994).

D. Kantoci, et al., "A Convenient Synthetic Route to the Disaccharide Repeating-Unit of Peptidoglycan", *Carbohydrate Research*, 162, pp. 227-235 (1987).

* cited by examiner

GLYCOPEPTIDE AND PREPARATION THEREOF

This is the national phase application, under 35 USC 371, for PCT/US01/12630, filed 18 Apr. 2001, which claims the priority of 60/197,237, filed 18 Apr. 2000 and, 60/255,829, filed 15 Dec. 2000.

FIELD OF THE INVENTION

The present invention relates to the stereospecific synthesis of a glycopeptide using a triply orthogonal protection scheme, in particular, the synthesis of N-acetylglucosaminyl - β-[1,4]-N-acetylmuramylmonopeptide and derivatives thereof.

BACKGROUND OF THE INVENTION

U.S. Pat. No. 4,395,399 to Ovchinnikov et al. disclosed glycopeptides of formula I

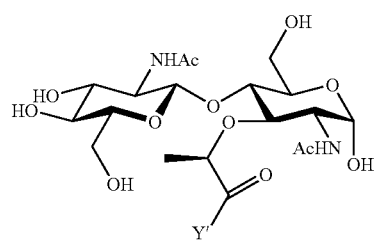

wherein Y' is a residue of an aminoacid or linear peptide of 2 to 5 amino acid residues. These glycopeptides are prepared by coupling unblocked muramyl-containing N-acetylaminosugars of formula II

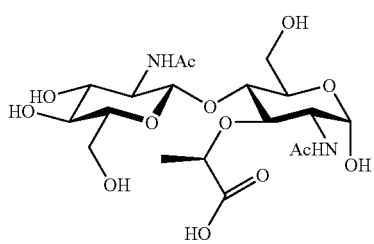

with blocked aminoacids or peptides. The disaccharide acid of formula II is obtained from large-scale fermentation of the bacterium *Micrococcus lysodeicticus*. The peptide portion is produced by conventional synthetic methods.

Compounds of formula I (hereinafter referred to as "Ovchinnikov glycopeptides"), particularly N-acetylglucosaminyl-N-acetylmuramyl-L-alanyl-D-isoglutamine (GMDP) and N-acetylglucosaminyl-N-acetylmuramyl-L-alanyl-D-glutamic acid (GMDP-A), are orally-active immunomodulators for use in a number of indications. (see, e.g., Ivanov, V. T., et al., *Immunologiya* No. 2, 4–5 (1996); Adrianova, I. E., et al., *Radiobiologiia* 32, 566–70 (1992); Palache, A. M., et al., *Vaccine* 14, 1327–30 (1996); and Khaitov, R. M., et al., "Immunotheraphy of Infections," Ed. Masihi, N., 205–211 (Marcel Dekker, Inc., 1994)). For example, compounds of formula I possess adjuvant activity. Adjuvants are compounds causing non-specific stimulation of the immune system in human beings and animals, resulting in an increased production of antibodies and enhancement of protective reaction of the organism against infection. Adjuvants are used in medicine for the manufacture of vaccines and sera. In addition, U.S. Pat. No. 5,506,204 to R. Aston discloses the use of GMDP and GMDP-A for treatment of septic shock.

The semi-synthetic approach for preparing glycopeptides of formula I described above is utilized because the disaccharide core, N-acetyl-(2-deoxy-2-aminoglucopyranosyl)-β-[1,4]-N-acetylmuramic acid, is one of the most difficult glucopyranosyl-glucopyranose disaccharides to synthesize. For example, the order of glucopyranose hydroxyl acceptor reactivity toward glycosyl cation donors, independent of donor source, is water>>ethanol>C(6)OH>C(2)OH>C(3)OH> the required C(4)OH. In addition, 2-deoxy-2-acylaminoglucopyranose C(4)OH acceptors are deactivated electronically relative to glucose itself. Muramic acid derivatives, in particular, suffer still further acceptor reactivity disadvantage due to steric crowding around the C(4) oxygen. Formation of the desired β-[1,4]-glycosidic bond requires a 2-deoxy-2-aminoglucopyranose glycosyl cation donor with a nitrogen substituent that will favor equatorial approach of the very modestly nucleophilic C(4)OH of a muramic acid derivative.

Several approaches to this formidable glycosidation problem have been documented. (see, e.g., Mercer, C., et al., *Tetrahedron Lett.* 13, 1029 (1973); Durette, P. L., et al., *Carbohydr. Res.*, 77, C1 (1979); Kusumoto, D., et al., *Bull. Chem. Soc. Jpn.*, 59, 1411 (1986); Kusumoto, D., et al., *Bull. Chem. Soc. Jpn.*, 59, 1419 (1986); Farkas, J., et al., *Carbohydr. Res.*, 163, 63 (1987); Kinzy, W., et al., *Liebigs Ann. Chem.*, 407 (1987) ; Termin, A., et al., *Liebigs Ann. Chem.*, 789 (1989); Ledvina, M., et al., *Collect. Czech. Chem. Commun.*, 54, 2784 (1989) and Termin, A., et al., *Liebigs Ann. Chem.*, 527 (1992). However, none of these approaches provides a process for preparing the disaccharide in sufficient amounts to be useful as an intermediate in the preparation of glycopeptides of formula I.

SUMMARY OF THE INVENTION

The present invention provides a process for preparing a protected glycopeptide of formula 1

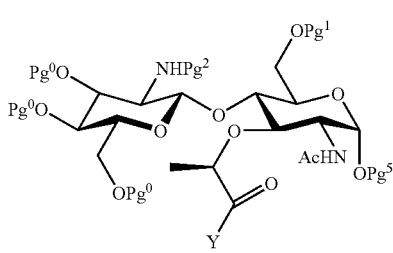

by coupling a muramylamide compound of formula 2

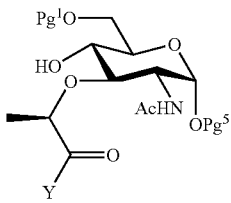

with a glucopyranosyl compound of formula 3

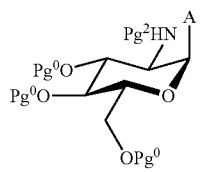

to form the protected glycopeptide of formula 1, wherein:
A is Br or Cl;
$Pg^0$ is an acyl hydroxy-protecting group;
$Pg^1$ is a hydroxy-protecting group which is not electron withdrawing;
$Pg^2$ is an amine-protecting group which does not lead to oxazoline formation;
$Pg^5$ is a hydroxy-protecting group;
$Pg^0$, $Pg^1$, $Pg^2$, and $Pg^5$ are mutually orthogonal protecting groups; and
Y is a residue of an amino acid or peptide, wherein:
Y forms an amide linkage with the attached carbonyl; and
Y comprises a protected terminal carboxy group.
The invention also provides compounds of formula III

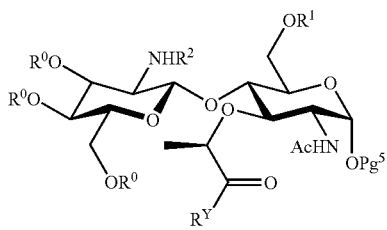

wherein:
$R^0$ is $Pg^0$ or hydrogen;
$R^1$ is $Pg^1$, $Pg^3$ or hydrogen;
$R^2$ is $Pg^2$ or acetyl;
$R^Y$ is Y or Y';
$Pg^0$ is an acyl hydroxy-protecting group;
$Pg^1$ is a hydroxy-protecting group which is not electron-withdrawing;
$Pg^2$ is a an amine-protecting group which does not lead to oxazoline formation;
$Pg^3$ is an acyl hydroxy-protecting group;
$Pg^5$ is a hydroxy-protecting group;
$Pg^0$, $Pg^1$, $Pg^2$ and $Pg^5$ are mutually orthogonal protecting groups;
Y' is a residue of an amino acid or peptide, wherein:
Y' forms an amide linkage with the attached carbonyl; and
Y comprises an unprotected terminal carboxy group;
Y is a residue of an amino acid or peptide, wherein:
Y forms an amide linkage with the attached carbonyl; and
Y comprises a protected terminal carboxy group.

Compounds of formula III are useful intermediates in the synthesis of the Ovchinnikov glycopeptides.

DETAILED DESCRIPTION

Definitions

As used above, and throughout the description of the invention, the following abbreviations, unless otherwise indicated, shall be understood to have the following abbreviations:

| Designation | Reagent or Fragment |
| --- | --- |
| Ac | —C(O)CH$_3$ |
| AcOH | acetic acid |
| Ac$_2$O | acetic anhydride |
| BOC | t-butyloxycarbonyl |
| DBU | 1,8-diazabicyclol[5.4.0]undec-7-ene |
| THF | tetrahydrofuran |
| TsOH | p-toluenesulfonic acid |
| NMM | N-methylmorpholine |
| TFA | trifluoroacetic acid |
| Troc | 2,2,2-trichioroethoxycarbonyl |
| min | minutes |
| h | hour(s) |
| Cbz | benzyloxycarbonyl |
| TLC | thin layer chromatography |
| NMR | nuclear magnetic resonance |
| ESI-MS | electro-spray ionization mass spectum |
| EtOAc | ethyl acetate |
| IR | infrared spectrum |
| MeOH | methanol |
| NaOMe | sodium methoxide |
| NHS | N-hydroxysuccinimide |
| EDCI | 1-[3-(dimethylamino)propyl]-3-ethylcarbodiimide hydrochloride |

As used above, and throughout the description of the invention, the following terms, unless otherwise indicated, shall be understood to have the following meanings:

"Amino acid" means an amino acid selected from the group consisting of natural and unnatural amino acids as defined herein. Amino acid is also meant to include-amino acids having L or D stereochemistry at the α-carbon. Preferred amino acids are those possessing an α-amino group. The amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are α-amino acids. Exemplary natural amino acids are isoleucine, proline, phenylalanine, tryptophan, methionine, glycine, serine, threonine, cysteine, tyrosine, asparagine, glutamine, lysine, arginine, histidine, aspartic acid and glutamic acid. Unnatural amino acid" means an amino acid for which there is no nucleic acid codon. Examples of unnatural amino acids include, for example, the D-isomers of the natural α-amino acids as indicated above; Aib (aminobutyric acid), βAib (3-amino-isobutyric acid), Nva (norvaline), βAla, Aad (2-aminoadipic acid), βAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), aIle (allo-isoleucine), Nle (norleucine), tert-Leu, Cit (citrulline), Orn, Dpm (2,2'-diaminopimelic acid), Dpr (2,3-diaminopropionic acid), α- or β-Nal, Cha (cyclohexyl-Ala), hydroxyproline, Sar (sarcosine), and the like; cyclic amino acids; $N^\alpha$-alkylated amino acids such as MeGly ($N^\alpha$-methylglycine), EtGly ($N^\alpha$-ethylglycine) and EtAsn ($N^\alpha$-ethylasparagine); and amino acids in which the α-carbon bears two side-chain substituents. The names of natural and unnatural amino acids and residues thereof used herein follow the naming conventions suggested by the IUPAC Commission on the Nomenclature of Organic Chemistry and the IUPAC-IUB Commission on Biochemical Nomenclature as set out in "Nomenclature of a-Amino Acids (Recommendations, 1974)" Biochemistry, 14(2), (1975). To the extent that the names and abbreviations of amino acids and residues thereof employed in this specification and appended claims differ from those noted, differing names and abbreviations will be made clear.

"Amino acid protecting group" and "peptide-protecting group" mean a group that protects an acid or amine moiety of the amino acid/peptide or other reactive moiety on the side chain of an amino acid/amino acid residue, e.g., hydroxy or thiol. For examples of "corresponding protected derivatives" of amino acid side chains, see T. W. Green and P. G. M. Wuts in "Protective Groups in Organic Chemistry" John Wiley and Sons, 1991. Protecting groups for an acid group in an amino acid are described herein in the section "carboxy-protecting group." Protecting groups for an amine group in an amino acid are described in the section "amine-protecting group."

"Amino acid residue" means the individual amino acid units incorporated into a peptide, or peptide portion of a molecule, through an amide linkage.

"Amine-protecting group" means an easily removable group that is known in the art to protect an amino group against undesirable reaction during synthetic procedures and to be selectively removable. The use of amine-protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. Amine protecting group also includes acid-labile amine-protecting groups (e.g., BOC) and hydrogenation-labile amine-protecting groups (e.g., Cbz). In the present invention, $Pg^2$ is a group which does not lead to the generation of undesirable oxazoline by-products (i.e., $Pg^2$ cannot be an acyl group). Suitable amine-protecting groups include carbamate and imide groups. Particular imide groups include phthalimide, tetrachlorophthalimide and $(Ac)_2N$—. Particular carbamate groups include methoxy-carbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, t-butyloxycarbonyl (BOC), 1,1-dimethyl-propynyloxycarbonyl, benzyloxycarbonyl (CBZ), p-nitrobenzyloxycarbonyl, 2,4-dichloro-benzyloxycarbonyl, trimethylsilyloxycarbonyl, 2,2,2-trichloroethoxycarbonyl, 1,1-dimethyl-2,2,2-trichloroethoxycarbonyl, and the like. A preferred amine-protecting group is 2,2,2-trichloroethoxycarbonyl.

"Carboxy-protecting group" means an easily removable group that is known in the art to protect an acidic hydrogen of a carboxyl group against undesirable reaction during synthetic procedures, e.g., to block or protect the acid functionality while the reactions involving other functional sites of the compound are carried out, and to be selectively removable. Such acid protecting groups are well known to those skilled in the art, having been extensively used in the protection of carboxyl groups, as described in U.S. Pat. Nos. 3,840,556 and 3,719,667, the disclosures of which are hereby incorporated herein by reference. For suitable acid protecting groups, see T. W. Green and P. G. M. Wuts in "Protective Groups in Organic Chemistry" John Wiley and Sons, 1991. Acid protecting group also includes hydrogenation labile acid protecting groups, such as benzyl. Examples of acid protecting groups include esters such as substituted and unsubstituted $C_1$ to $C_8$ alkyl, e.g., methyl, ethyl, t-butyl, methoxymethyl, methylthiomethyl, 2,2,2-trichloroethyl and the like, tetrahydropyranyl, substituted and unsubstituted phenylalkyl such as benzyl and substituted derivatives thereof such as alkoxybenzyl or nitrobenzyl groups and the like, cinnamyl, dialkylaminoalkyl, e.g., dimethylaminoethyl and the like, trimethylsilyl, substituted and unsubstituted amides and hydrazides, e.g., amides and hydrazides of N,N-dimethylamine, 7-nitroindole, hydrazine, N-phenylhydrazine and the like, acyloxyalkyl groups such as pivaloyloxymethyl or propionyloxymethyl and the like, aroyloxyalkyl such as benzoyloxyethyl and the like, alkoxycarbonylalkyl such as methoxycarbonylmethyl, cyclohexyloxycarbonylmethyl and the like, alkoxycarbonyloxyalkyl such as t-butyloxycarbonyloxymethyl and the like, alkoxycarbonylaminoalkyl such as t-butyloxycarbonylaminomethyl and the like, alkylaminocarbonylaminoalkyl, such as methylaminocarbonylaminomethyl and the like, acylaminoalkyl such as acetylaminomethyl and the like, heterocyclylcarbonyloxyalkyl such as 4-methylpiperazinyl-carbonyloxymethyl and the like, dialkylaminocarbonylalkyl such as dimethylaminocarbonyl-methyl and the like, (5-(lower alkyl)-2-oxo-1,3-dioxolen-4-yl)alkyl such as (5-t-butyl-2-oxo-1,3-dioxolen-4-yl)methyl and the like, and (5-phenyl-2-oxo-1,3-dioxolen-4-yl)alkyl such as (5-phenyl-2-oxo-1,3-dioxolen-4-yl)methyl and the like. Particular carboxy-protecting groups include methyl, 9-fluorenylmethyl, 2-(trimethylsilyl)ethyl, 2-(trimethylsilyl)ethoxymethyl, 2-methylthioethyl, 1,3-dithianyl-2-methyl, 2-(p-toluenesulfonyl)ethyl, 2-(p-nitrophenylsulfenyl)ethyl. 2-(2'-pyridyl)ethyl, 2-(diphenylphosphino)ethyl, p-(methylmercapto)phenyl, nitroethyl, allyl and the like. Preferred carboxy-protecting groups are cyanoethyl, t-butyl and —$CH_2CH_2SO_2Ph$.

"Hydroxy-protecting group" means an easily removable group that is known in the art to protect an hydroxyl group against undesirable reaction during synthetic procedures and to be selectively removable. The use of hydroxy-protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. In the present invention, the $Pg^0$, $Pg^1$, and $Pg^5$ hydroxy-protecting groups are mutually orthogonal, as described herein. $Pg^1$ cannot be an electron-withdrawing group, since such groups deactivate the coupling reaction between the muramylamide compound of formula 2 and glucosopyranosyl compound of formula 3. Suitable $Pg^1$ groups include aralkyl, aralkenly and silyl groups. Particular aralkyl and alkenyl groups include benzyl and allyl, respectively. Particular silyl groups include trialkylsilyl groups, such as trimethylsilyl and (t-butyl)dimethylsilyl. Preferred $Pg^1$ groups are allyl and benzyl; a more preferred group is benzyl. In addition, $Pg^0$ and $Pg^3$ must be removable by saponification (i.e., $Pg^0$ and $Pg^3$ must be acyl groups). Particular acyl groups include formyl, acetyl, chloroacetyl, trichloroacetyl, o-nitrophenylacetyl, o-nitrophenoxy-acetyl, trifluoroacetyl, acetoacetyl, 4-chlorobutyryl, isobutyryl, o-nitrocinnamoyl, picolinoyl, acylisothiocyanate, aminocaproyl, benzoyl, and the like. Preferred groups are chloroacetyl and acetyl; a more preferred group is acetyl. Finally, since $Pg^5$ is orthogonal to the other hydroxy-protecting groups, it must be stable under saponification conditions (i.e., $Pg^5$ cannot an acyl group) and some conditions suitable for removal of $Pg^1$. Suitable $Pg^5$ groups aralkyl and alkenyl groups. Preferred $Pg^5$ groups include allyl, n-pentenyl, and benzyl; a more preferred group is benzyl.

"Leaving group" of an activated ester means a substituent having sufficient lability such that it can be substituted by a good nucleophile (i.e., an amino group of a peptide unit). The lability of a particular substituent will vary depending upon substituents on the same and/or adjacent carbon atoms and the nature of the leaving group. Those skilled in the art will appreciate the types of leaving groups capable of substitution by an amino nucleophile. For suitable leaving groups, see M. Bodanszky and A. Bodanszky in "The Practice of Peptide Synthesis" Springer-Verlag, 1984; and M. Bodanszky in "Principles of Peptide Synthesis" Springer-Verlag, 1984. In the present invention, the leaving group activates the attached carbonyl such that the terminal amino acid group acts as a linker for linking the disaccharide with the peptide unit. Particular leaving groups include pentafluorophenoxy, N-oxysuccimide, N-oxyphthalimide, and N-oxybenzotriazole. A preferred leaving group is N-oxysuccinimide.

"Orthogonal protecting groups" means protecting groups for which there exists a set of conditions wherein one of the groups can be removed without removing the other(s). The term encompasses protecting groups for different moieties (e.g., orthogonal amine and hydroxy protecting groups) as well as the same moiety (e.g., orthogonal hydroxy-protecting groups). It is not a requirement that orthogonal protecting groups necessarily be different. For example, when the term is used to describe protecting groups for the same moiety, the groups may be different (e.g., orthogonal acetyl and benzyl hydroxy-protecting groups) or the same (e.g., orthogonal benzyl protecting groups). "Electron-withdrawing group" means a group which is a more powerful electron attractor than hydrogen. Electron withdrawing groups exhibit negative inductive effects, whereas groups which are poorer electron attractors than hydrogen exhibit positive inductive effects. (see, e.g., E. S. Gould, Mechanism and Structure in Organic Chemistry, Holt, Rinehart and Winston, New York (1959), incorporated herein by reference).

"Acyl" means an R—C(O)— group, wherein R is bonded to the CO group through a carbon-carbon bond.

"Alkyl" means an aliphatic hydrocarbon group which may be straight or branched having about 1 to about 20 carbon atoms in the chain. Preferred alkyl groups have 1 to about 12 carbon atoms in the chain, more preferred is lower alkyl as defined herein. Branched means that one or more lower alkyl groups such as methyl, ethyl or propyl are attached to a linear alkyl chain. "Lower alkyl" means about 1 to about 4 carbon atoms in the chain that may be straight or branched.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain that may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Aryl" means an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

"Carboxy" means an HO(O)C— (carboxylic acid) group.

"N-oxysuccinimide" means a moiety of the following

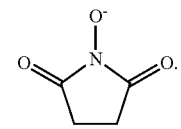

structure

"Peptide" means a polymer encompassing amino acid residues joined together through amide bonds.

"GMDP" refers to N-acetylglucosaminyl-N-acetylmuramyl-L-alanyl-D-isoglutamine, which has the following structure:

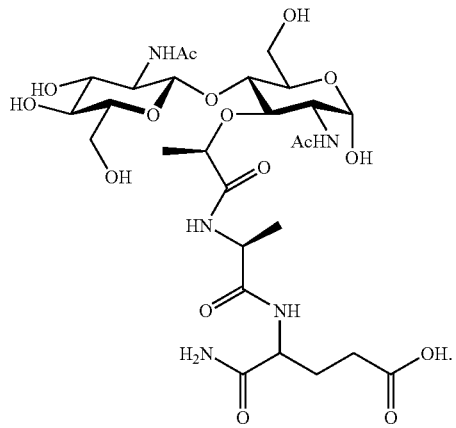

"GMDP-A" refers to the N-acetylglucosaminyl-N-acetylmuramyl-L-alanyl-D-glutamic acid, which has the following structure:

Embodiments

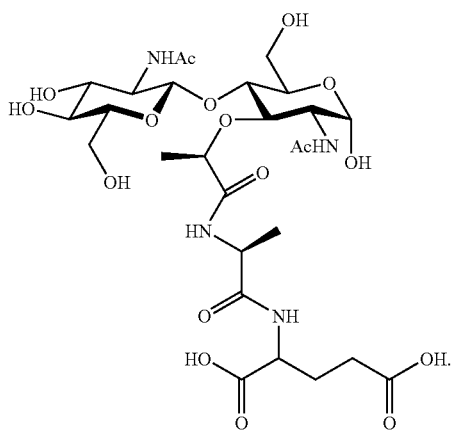

With reference to formulas 1–19, as described herein, particular and preferred embodiments are as follows:

In a first particular embodiment of the invention, the muramylamide compound of formula 2, as described herein, and glucopyranosyl compound of formula 3, as described herein, are reacted under scrupulously anhydrous conditions.

In a second particular embodiment of the invention, $Pg^0$ is acetyl.

In a third particular embodiment of the invention, the $Pg^0$ group of a compound of formula 8, as described herein, is removed to form a compound of formula 7, as described herein.

In a fourth particular embodiment of the invention, the $Pg^0$ group of a compound of formula 13, as described herein, is removed to form a compound of formula 12, as described herein.

In a preferred embodiment, the $Pg^0$ group is removed in the presence of aqueous sodium hydroxide.

In a fifth particular embodiment of the invention, $Pg^5$ is benzyl, allyl or n-pentenyl.

In a preferred embodiment, $Pg^5$ is benzyl.

In a sixth particular embodiment of the invention, the $Pg^5$ group of a compound of formula 12, as described herein, is removed to form a compound of formula 11, as described herein.

In a seventh particular embodiment of the invention, the $Pg^5$ group of a compound of formula 7, as described herein, is removed to form a compound of formula I, as described herein.

In a preferred embodiment, the $Pg^5$ group is removed in the presence of hydrogen and a palladium/carbon catalyst.

In an eighth particular embodiment of the invention, $Pg^1$ is a benzyl, allyl or silyl hydroxy-protecting group;

In a preferred embodiment, $Pg^1$ is benzyl.

In a preferred embodiment, a muramylamide compound of formula 3a, as described herein, is prepared by reductively opening the 1,3-dioxane ring of a muramylamide of formula 6, as described herein.

In a ninth particular embodiment of the invention, the $Pg^1$ group of a compound of formula 1, as described herein, is exchanged with a $Pg^3$ group to form a compound of formula 10, as described herein.

In a tenth particular embodiment of the invention, the $Pg^1$ group of a compound of formula 1a, as described herein, is exchanged with a $Pg^3$ group to form a compound of formula 19, as described herein.

In a preferred embodiment, $Pg^3$ is acetyl.

In a more preferred embodiment, the exchanging is carried out in the presence of acetic anhydride, acetic acid, and zinc chloride.

In a eleventh particular embodiment of the invention, $Pg^2$ is a carbamate or imide amine-protecting group;

In a preferred embodiment, $Pg^2$ is 2,2,2-trichloroethoxycarbonyl.

In an twelfth particular embodiment of the invention, the $Pg^2$ group of a compound of formula 19, as described herein, is exchanged with an acetyl group to form a compound of formula 18, as described herein.

In a thirteenth particular embodiment of the invention, the $Pg^2$ group of a compound of formula 10, as described herein, is exchanged with an acetyl group to form a compound of formula 9, as described herein.

In a preferred embodiment, the exchanging is carried out in the presence of acetic anhydride, acetic acid, and zinc dust.

In a fourteenth particular embodiment of the invention, the $Pg^3$ group of a compound of formula 8, as described herein, is removed to form a compound of formula 7, as described herein.

In a fifteenth particular embodiment of the invention, the $Pg^3$ group of a compound of formula 13, as described herein, is removed to form a compound of formula 12, as described herein.

In a preferred embodiment, the $Pg^3$ group is removed in the presence of aqueous sodium hydroxide.

In a sixteenth particular embodiment of the invention, LOH is N-hydroxysuccinimide.

In a seventeenth particular embodiment of the invention, A is Br.

In an eighteenth particular embodiment of the invention, Y is a peptide comprising 2 to 5 amino acid residues.

In a preferred embodiment, Y is a linear peptide.

In an nineteenth particular embodiment of the invention, each of X' and W' is a residue of an amino acid or peptide comprising 2 to 4 amino acid residues, provided that the total number of amino acid residues in X' and W' is 2 to 5;

In a preferred embodiment, each of X' and W' is a linear peptide.

In a more preferred-embodiment, the —X'—W' is a linear peptide;

With reference to formula III above, particular and preferred embodiments are as follows:

In a twentieth particular embodiment of the invention, $R^0$ is $Pg^0$.

In a preferred embodiment, $Pg^0$ is acetyl.

In a twenty-first particular embodiment of the invention, $R^0$ is hydrogen.

In a twenty-second particular embodiment of the invention, $R^1$ is $Pg^1$.

In a preferred embodiment, $Pg^1$ is benzyl, allyl or silyl.

In a more preferred embodiment, $Pg^1$ is benzyl.

In a twenty-third particular embodiment of the invention, $R^1$ is $Pg^3$.

In a preferred embodiment, $Pg^3$ is acetyl.

In a twenty-fourth particular embodiment of the invention, $R^1$ is hydrogen.

In a twenty-fifth particular embodiment of the invention, $R^2$ is $Pg^2$.

In a preferred embodiment, $Pg^2$ a carbamate or imide amine-protecting group;

In more preferred embodiment, $Pg^2$ is 2,2,2-trichloroethoxycarbonyl.

In a twenty-sixth particular embodiment of the invention, $R^2$ is acetyl.

In a twenty-seventh particular embodiment of the invention, $Pg^5$ is benzyl, allyl or n-pentenyl.

In a preferred embodiment, $Pg^5$ is benzyl.

In a twenty-eighth particular embodiment of the invention, Y is a peptide comprising 2 to 5 amino acid residues.

In a preferred embodiment, Y' is a linear peptide.

In a twenty-ninth particular embodiment of the invention, Y' is a peptide comprising 2 to 5 amino acid residues.

In a preferred embodiment, Y' is a linear peptide.

This invention also includes all combinations of particular and preferred embodiments described herein.

Preparation of Compounds of Formula 1

Synthesis of a compound of formula 1, the central disaccharide core, in orthogonally protected form presents a significant synthetic challenge. For example, identification of a protective scheme having triple orthogonality is highly desirable to accomplish selective unmasking of the three types of pendant hydroxyl groups (i.e., anomeric OH, peripheral OH, and carboxyl OH). In addition, the stereoselective construction of the β-[1,4] glycosidic linkage is expected to be difficult irrespective of the method used to generate a reactive glycosyl cation donor. For example, with respect to the glycosyl cation, each of the following inherent properties contribute to a loss of reactivity of the glycosyl cation acceptor: (i) the intrinsic lack of nucleophilicity of the C(4)-hydroxyl group of glucopyranose-based acceptors, (ii) additional steric crowding around the C(4)-hydroxyl-of muramic acid-based acceptors, and (iii) additional electronic deactivation of 2-deoxy-2-acylaminoglucopyranose acceptors relative to their glucopyranose-based counterparts. With respect to the glycosyl cation donor, an activation method with a predisposition toward formation of a β-[1,4] glycosidic linkage is needed. The reaction conditions for glycosyl cation generation also needs to be compatible with functionality resident in both the donor and acceptor.

A compound of formula 1, wherein the variables are as described herein, may be prepared by coupling a muramylamide compound of formula 2, wherein the variables are as

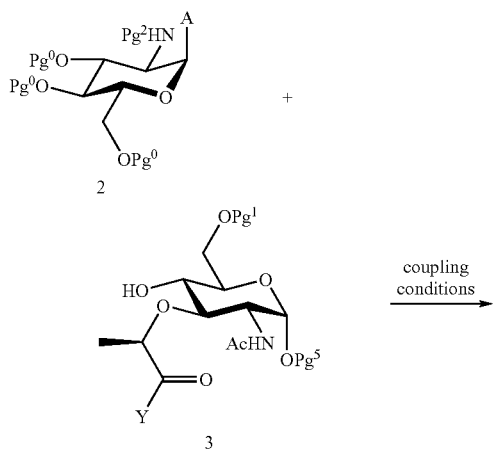

-continued

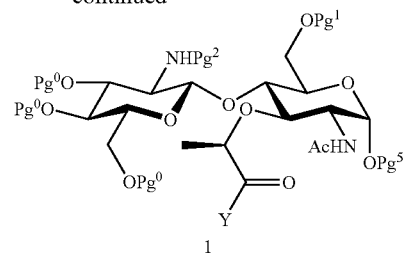

described herein, with a glucopyranosyl compound of formula 3, wherein the variables are as described herein, under appropriate conditions. Particular conditions include carrying out the coupling reaction under scrupulously anhydrous Konigs-Knorr conditions (e.g., in a silver triflate/dichloromethane solution including molecular sieves), or the like.

A compound of formula 2 is prepared according to the procedures described in Imoto, M., Bull. Chem. Soc. Jpn., 60, 2205 (1987).

A compound of formula 3, wherein the variables are as described herein, may be prepared by coupling an acid of formula 4, wherein the variables are as described herein,

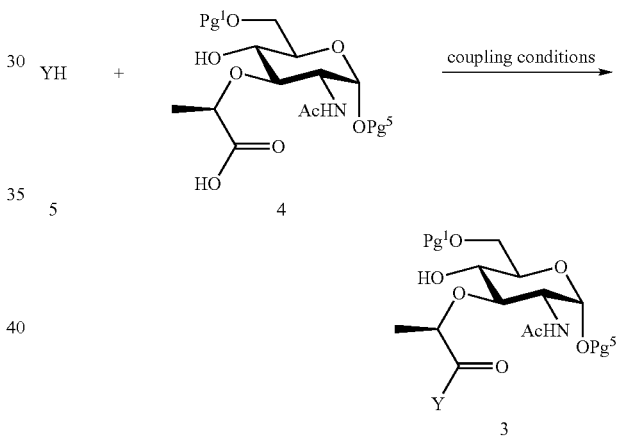

with a protected amino acid/peptide compound of formula 5, wherein Y is as described herein, under appropriate conditions. Particular conditions encompass carrying out the coupling reaction in a solution of NMM (or the like) and 2-chloro-4,6-dimethoxy-1,3,5-triazine (or the like) in $CH_2Cl_2$ (or the like), wherein the compound of formula 5 is added as the tosylate salt, or the like.

A compound of formula 3a, wherein $Pg^1$ is benzyl and the other variables are as described herein, may be prepared by treating a compound of formula 6, wherein the variables are -continued

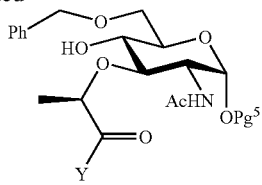

3a

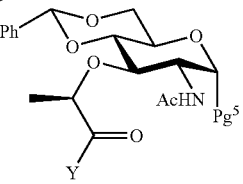

6 as defined herein, with a reducing agent under appropriate conditions. A particular reducing agent is triethylsilane, or the like. Particular conditions include carrying out the reduction in $CH_2Cl_2$ (or the like) and TFA (or the like) at about 0° C. This reaction provides an efficient means for regioselective introduction of the benzyl protection/activation at C(6) OH of the muramic acid derivative.

It is known that when an ester derivative of a compound of formula 6 is treated with trifluoroacetic acid and triethylsilane as described in DeNinno, M. P., et al., Tetrahedron Lett., 36, 669 (1995), only a small amount of the analogous compound of formula 3a is observed. The major product formed is a lactone, as shown in scheme I.

Scheme I

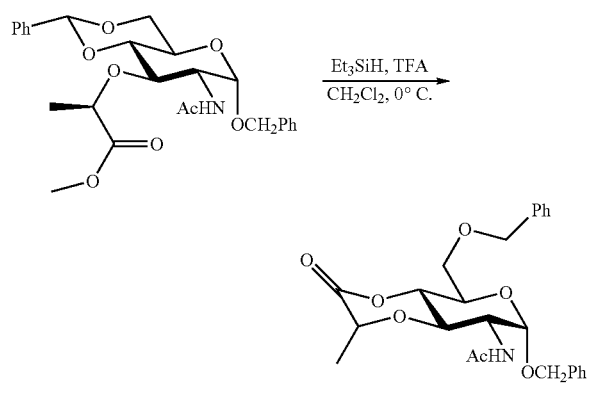

The acid-catalyzed lactonization proceeds at a rate competitive with the reductive ring opening, thus leading to the undesired lactone. In the present invention, however, introduction of an amide bond in place of the ester bond eliminates the conversion to the lactone, thus allowing the desired product (compound 3a) to be isolated in much higher yields.

A compound of formula 6, wherein the variables are as described herein, may be prepared by coupling an acid of formula 4a, wherein the variables are as described herein,

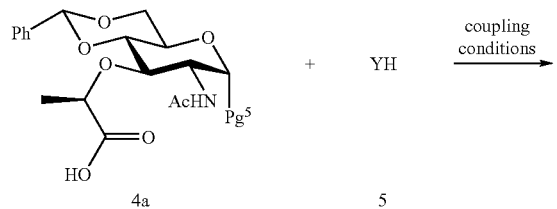

with a protected amino acid/peptide compound of formula 5, wherein Y is as described herein, under appropriate conditions. Particular conditions encompass carrying out the coupling reaction in a solution of NMM (or the like) and 2-chloro-4,6-dimethoxy-1,3,5-triazine (or the like) in $CH_2Cl_2$ (or the like), wherein the compound of formula 5 is added as the tosylate salt, or the like.

The synthesis of the core disaccharide outlined above provides a high throughput access to intermediates in the total synthesis of the Ovchinnikov glycopeptides. Due to the convergent approach, protecting group economy, and crystalline nature of the intermediates, one can easily scale the process to substantial or commercial volumes.

Preparation of Compounds of Formula I

I. Direct Attachment of the Amino Acid/Peptide Portion

A Compounds of formula I, wherein Y' is the unprotected form of Y, may be prepared by removing the $Pg^5$ group of a compound of formula 7, wherein the variables are as described herein, in the presence of a hydroxy-deprotecting agent and under appropriate conditions.

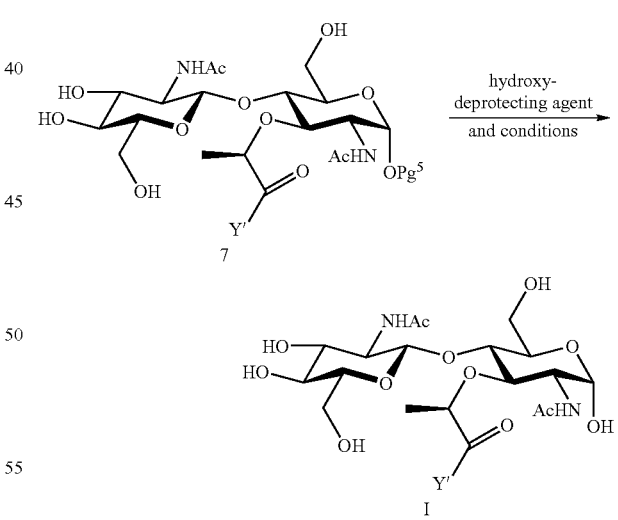

A particular $Pg^5$ group is benzyl, or the like. A particular hydroxy-deprotecting agent is $H_2/(Pd/C)$, or the like. Particular hydroxy-deprotecting conditions encompass carrying out the deprotection in an alcohol solvent (e.g., methanol, ethanol or the like) at about room temperature.

A compound of formula 7, wherein the variables are as described herein, may be prepared by saponifying the $Pg^0$ and $Pg^3$ groups of a compound of formula 8,

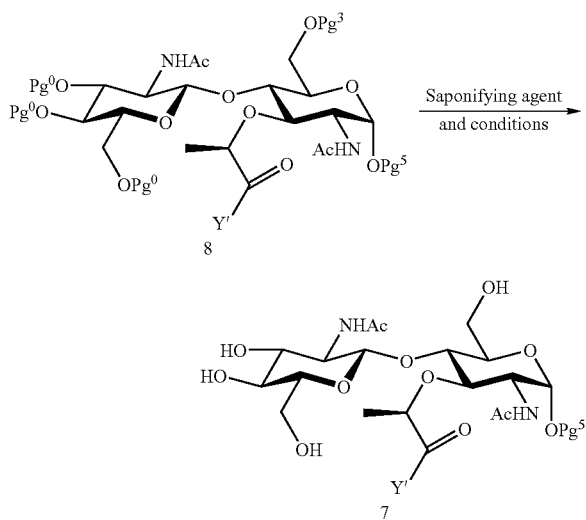

wherein Pg³ is an acyl hydroxy-protecting group and the other variables are as described herein, in the presence of a saponifying agent and under appropriate conditions. A particular Pg⁰ and Pg³ group is acetyl, or the like. A particular saponifying agent is aqueous sodium hydroxide, or the like. Particular saponifying conditions encompass carrying out the saponification in an alcohol solvent (e.g., methanol, ethanol or the like) at about room temperature.

A compound of formula 8, wherein the variables are as defined herein, may be prepared by deprotecting the Y group a compound of formula 9, wherein the variables are as described herein, under appropriate conditions. The peptide-deprotecting is carried out using an appropriate deprotecting agent that depends on the nature of the peptide-protecting group, i.e., whether it is removable (labile) under acid, base, or hydrogenation conditions, and other reactive moieties in

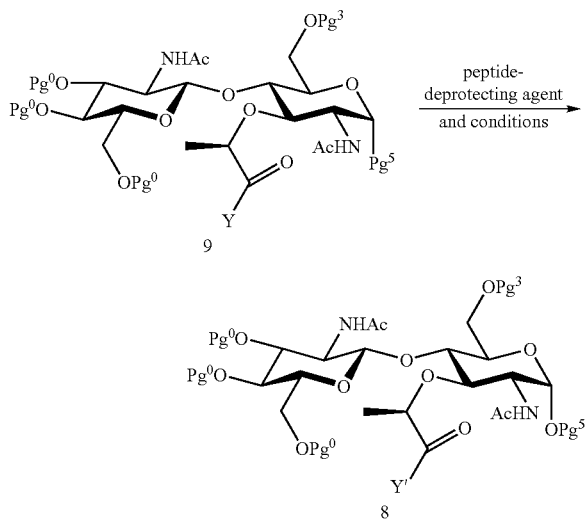

the compound undergoing deprotection, i.e., a deprotecting agent is chosen to carry out the deprotection without affecting the other reactive moieties unless a concomitant reaction is desired. A particular peptide-protecting group for a carboxylic acid moiety is $C_1$ to $C_8$ alkyl; more particularly t-butyl, or the like. A particular peptide-deprotecting agent for such a group is an inorganic acid; more particularly HCl, or the like. Another particular peptide-protecting group for a carboxylic acid moiety is $—CH_2CH_2SO_2Ph$, or the like. A particular peptide-deprotecting agent for such a group is DBU (or the like), wherein particular conditions encompass dissolving the compound of formula 9 in THF (or the like) and adding DBU (or the like) dropwise as a THF solution (or the like).

A compound of formula 9, wherein the variables are as described herein, may be prepared by exchanging the Pg² group of compound of formula 10, wherein the variables are as described herein, with an acetyl group in the presence of

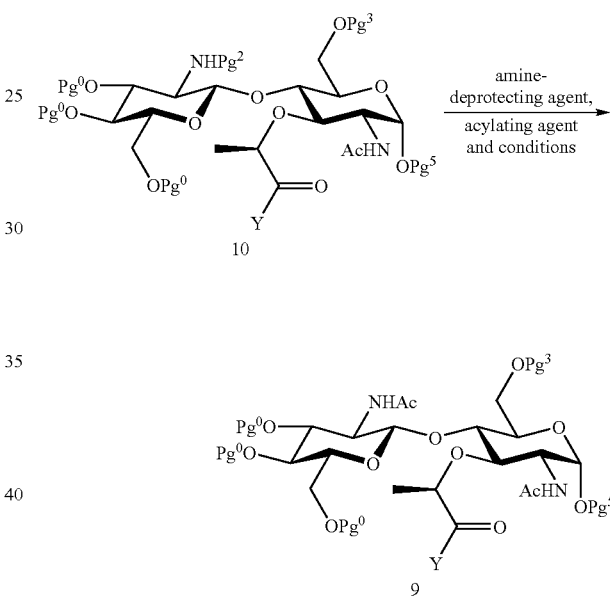

an amine-deprotecting agent and acylating agent under appropriate conditions. The amine-deprotecting is carried out using an appropriate deprotecting agent that depends on the nature of the amine-protecting group, i.e., whether it is removable (labile) under acid, base, or hydrogenation conditions, and other reactive moieties in the compound undergoing deprotection, i.e., a deprotecting agent is chosen to carry out the deprotection without affecting the other reactive moieties unless a concomitant reaction is desired. A particular amine-protecting group is β,β,β-trichloroethoxycarbonyl, or the like. A particular deprotecting agent is Zn dust (or the like) in the presence of a proton source (e.g., acetic acid or the like). A particular acylating agent is acetic anhydride, or the like. Particular conditions include adding Zn dust (or the like) and about a 3:2:1 mixture of THF:Ac₂O:AcOH (or the like) to a solution of the compound of formula 10 in about a 2:1 mixture of Ac₂O:AcOH, or the like.

A compound of formula 10, wherein the variables are as described herein, may be prepared by exchanging the Pg¹ group a compound of formula 1, wherein the other variables are as described herein, with a $Pg^3$ group in the presence

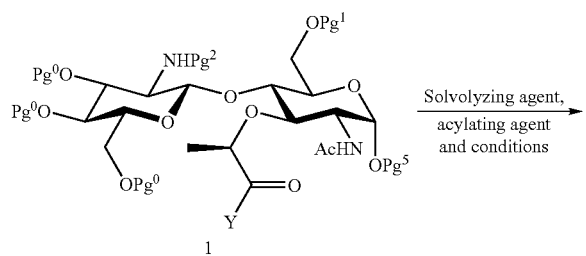

1

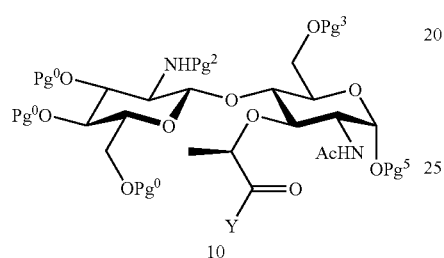

10 of a solvolyzing agent and acylating agent under appropriate conditions. The solvolysis is carried out using an appropriate solvolyzing agent that depends on the nature of the hydroxy-protecting group, i.e., a solvolyzing agent is chosen to carry out the solvolysis without affecting the other reactive moieties unless a concomitant reaction is desired. A particular hydroxy-protecting group is benzyl, or the like. A particular solvolyzing agent is $ZnCl_2$, or the like. A particular acylating agent is acetic anhydride, or the like. Particular conditions include carrying out the solvolysis/acylation in about a 2:1 mixture of $Ac_2O:AcOH$, or the like.

II. Attachment of the Amino Acid/Peptide Portion in Stages

A compound of formula I, wherein —Y' is —X'—W', X' is a residue of an amino acid or peptide which forms an amide linkage with the attached carbonyl, and W' is a residue of an amino acid or peptide, may be prepared by deprotecting the W group of a compound of formula 11 in the presence of a

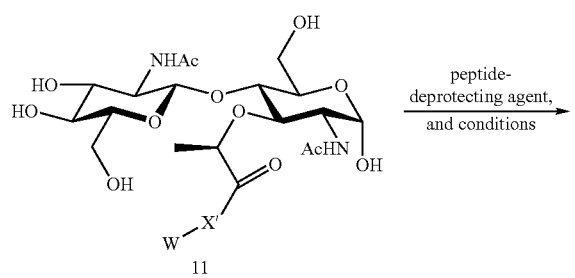

11

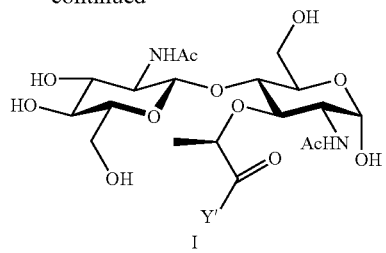

I peptide-deprotecting agent under appropriate conditions. The peptide-deprotecting is carried out using an appropriate deprotecting agent that depends on the nature of the peptide-protecting group, i.e., whether it is removable (labile) under acid, base, or hydrogenation conditions, and other reactive moieties in the compound undergoing deprotection, i.e., a deprotecting agent is chosen to carry out the deprotection without affecting the other reactive moieties unless a concomitant reaction is desired. A particular peptide-protecting group for a carboxylic acid moiety is $C_1$ to $C_8$ alkyl; more particularly t-butyl, or the like. A particular peptide-deprotecting agent for such a group is an inorganic acid; more particularly HCl, or the like. Another particular peptide-protecting group for a carboxylic acid moiety is —$CH_2CH_2SO_2Ph$, or the like. A particular peptide-deprotecting agent for such a group is DBU (or the like), wherein particular conditions encompass dissolving the compound of formula 11 in THF (or the like) and adding DBU (or the like) dropwise as a THF solution, or the like.

A compounds of formula 11 may be prepared by removing the $Pg^5$ group of a compound of formula 12, wherein the variables are as described herein, in the presence of a hydroxy-deprotecting agent and under appropriate conditions.

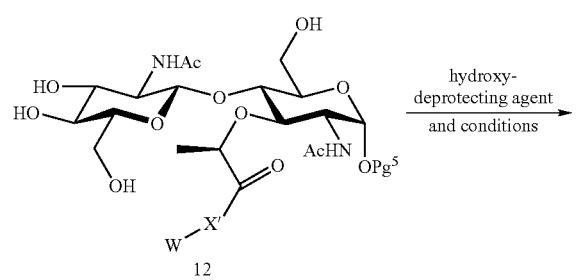

12

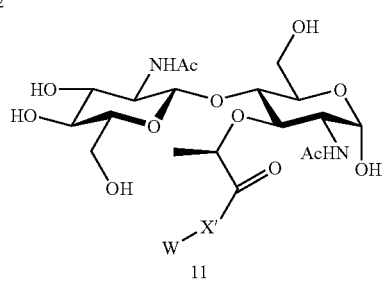

11

A particular protecting group is benzyl, or the like. A particular hydroxy-deprotecting agent is $H_2/(Pd/C$ carbon), or the like. Particular hydroxy-deprotecting conditions encompass carrying out the deprotection in an alcohol solvent (e.g., methanol, ethanol or the like) at about room temperature.

A compound of formula 12, wherein the variables are as described herein, may be prepared by saponifying the $Pg^0$ and $Pg^3$ groups of a compound of formula 13,

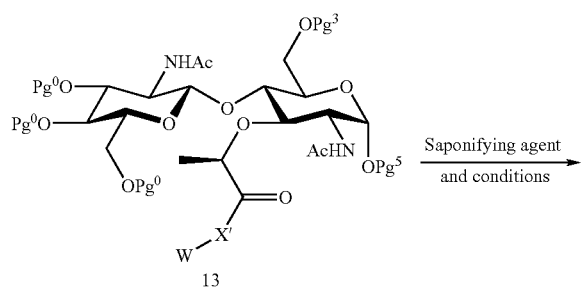

13

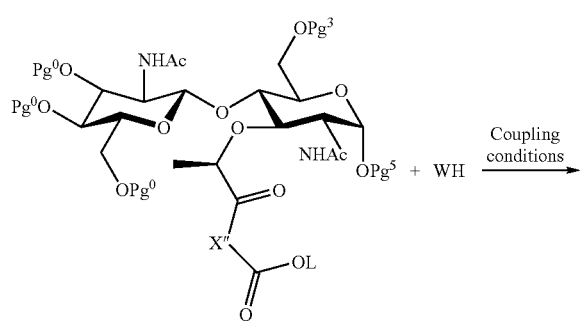

12 wherein the variables are as described herein, in the presence of a saponifying agent under appropriate conditions. A particular saponifying agent aqueous sodium hydroxide, or the like. Particular conditions encompass carrying out the saponification in an alcohol solvent (e.g., methanol, ethanol or the like) at about room temperature.

A compound of formula 13, wherein the variables are as described herein, may be prepared by coupling a compound of formula 15, wherein —X"C(O)OL is the activated ester of —X', —OL is a leaving group capable of substitution by an amino nucleophile, and the other variables area as described herein, with a protected amino acid/peptide of formula 14, wherein W is as defined herein, and under appropriate conditions.

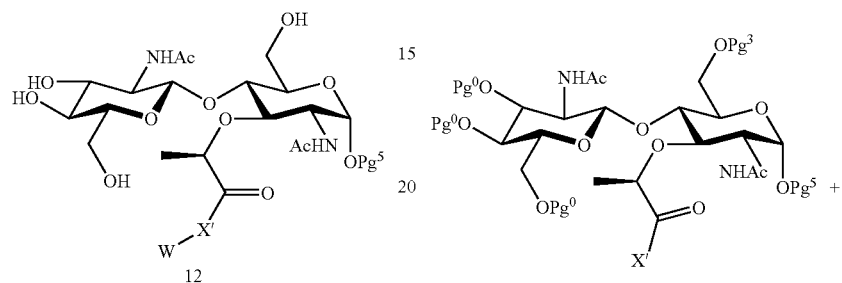

15          14

13

A particular protected amino acid is γ-Obu$^t$-iso-Gln, or the like. Particular conditions encompass adding dropwise a solution of γ-Obu$^t$-iso-Gln or the like (in about a 2:1 mixture of acetonitrile:DMF, or the like) to a solution of compound 15 (in acetonitrile or the like), followed immediately by diisopropylethyl amine, or the like.

A compound of formula 15, wherein the variables are as described herein, may be prepared by esterifying an acid of formula 17, wherein the variables are as defined herein, with a compound of formula 16, wherein the variables are as described herein, under appropriate conditions.

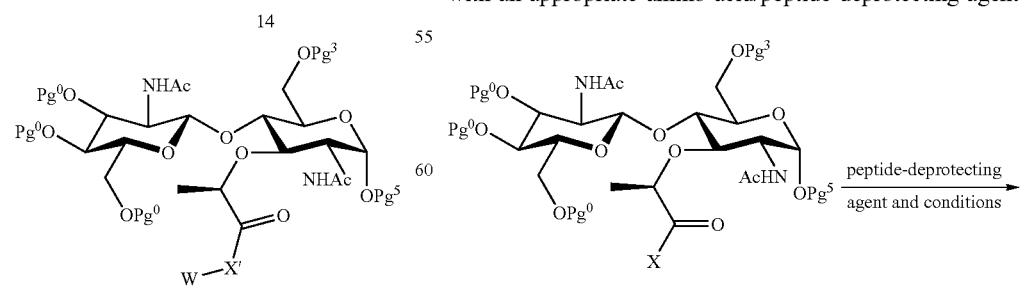

17

LOH  $\xrightarrow{\text{esterifying conditions}}$

16

15

A particular compound of formula 16 is N-hydroxysuccin-imide, or the like. Particular conditions encompass forming a slurry of the compound of formula 17 in acetonitrile (or the like), and adding EDCI (or the like) and N-hydroxysuccin-imnide (or the like) to the slurry at about room temperature.

A compound of formula 17, wherein the variables are as described herein, may be prepared by deprotecting the terminal carboxy moiety of the X group of a compound of formula 18, wherein the variables are as described herein, with an appropriate amino acid/peptide deprotecting agent

18

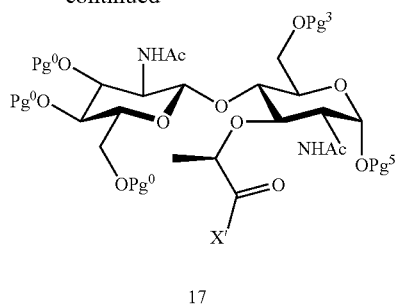

17 under appropriate conditions. The peptide-deprotecting is carried out using an appropriate deprotecting agent that depends on the nature of the carboxy-protecting group, i.e., whether it is removable (labile) under acid, base, or hydrogenation conditions, and other reactive moieties in the compound undergoing deprotection, i.e., a deprotecting agent is chosen to carry out the deprotection without affecting the other reactive moieties unless a concomitant reaction is desired. A particular peptide-protecting group for a carboxylic acid moiety is $C_1$ to $C_8$ alkyl; more particularly t-butyl, or the like. A particular peptide-deprotecting agent for such a group is an inorganic acid; more particularly HCl, or the like. Another particular peptide-protecting group for a carboxylic acid moiety is —$CH_2CH_2SO_2Ph$, or the like. A particular peptide-deprotecting agent for such a group is DBU (or the like), wherein particular conditions encompass dissolving the compound of formula 18 in THF (or the like) and adding DBU (or the like) dropwise as a THF solution, or the like.

A compound of formula 18, wherein the variables are as described herein, may be prepared by exchanging the $Pg^2$ group of a compound of formula 19, wherein the variables are as described herein, with an acetyl group in the presence of

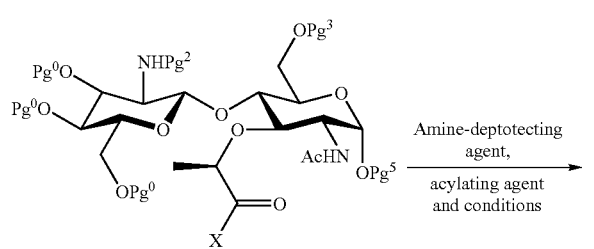

19

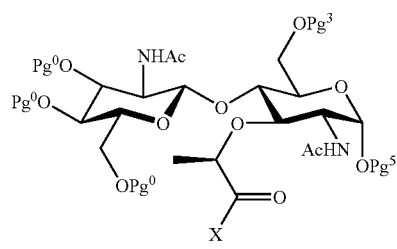

18 an amine-deprotecting agent and an acylating agent under the appropriate conditions. The amine-deprotecting is carried out using an appropriate deprotecting agent that depends on the nature of the amine-protecting group, i.e., whether it is removable (labile) under acid, base, or hydrogenation conditions, and other reactive moieties in the compound undergoing deprotection, i.e., a deprotecting agent is chosen to carry out the deprotection without affecting the other reactive moieties unless a concomitant reaction is desired. A particular amine-protecting group is β,β,β-trichloroethoxycarbonyl, or the like. A particular deprotecting agent is Zn dust (or the like) in the presence of a proton source (e.g., acetic acid or the like). A particular acylating agent is acetic anhydride, or the like. Particular conditions include adding Zn dust (or the like) and about a 3:2:1 mixture of THF:$Ac_2O$:AcOH (or the like) to a solution of the compound of formula 8 in about a 2:1 mixture of $Ac_2O$:AcOH, or the like.

A compound of formula 19, wherein the variables are as described herein, may be prepared by exchanging the $Pg^1$ group of a compound of formula 1a, wherein the variables are as described herein, with a $Pg^3$ group in the presence of a

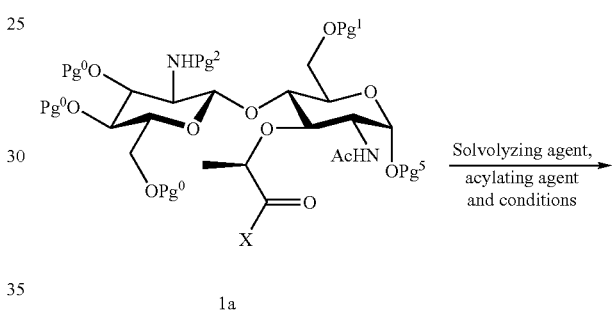

1a

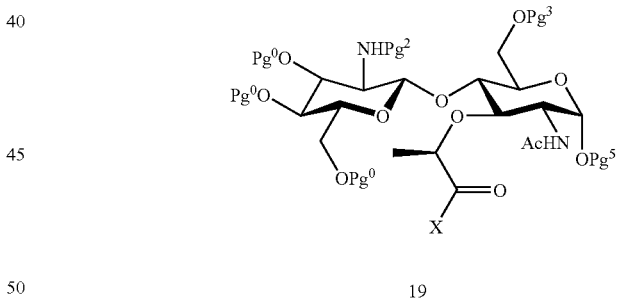

19 solvolyzing agent and acylating agent under appropriate conditions. The solvolysis is carried out using an appropriate solvolyzing agent that depends on the nature of the hydroxy-protecting group, i.e., a solvolyzing agent is chosen to carry out the solvolysis without affecting the other reactive moieties unless a concomitant reaction is desired. A particular hydroxy-protecting group is benzyl, or the like. A particular solvolyzing agent is $ZnCl_2$, or the like. A particular acylating agent is acetic anhydride, or the like. Particular conditions include carrying out the solvolysis/acylation in about a 2:1 mixture of $Ac_2O$:AcOH, or the like.

It is understood that the process described above can be modified so that the peptide portion can attached in three or more stages.

EXAMPLES

General

Reactions are carried out with continuous stirring under a positive pressure of nitrogen except where noted. Dilutions/solutions of liquids are shown as volume:volume. Reagents and solvents are purchased and used without further purification. TLC is performed with 0.25 mm silica gel 60 plates with a 254 nm fluorescent indicator from E. Merck. Plates are developed in a covered chamber and visualized by ultraviolet light or by treatment with 5% phosphomolybdic acid in ethanol followed by heating. Flash chromatography is carried out with silica gel 60, 230–400 mesh (0.040–0.063 mm particle size) purchased from EM Science. HPLC analyses and purifications are performed using Dynamax C8 columns with the specified solvent system and flow rate.

NMR spectra are reported as chemical shifts in parts-per-million (ppm) downfield from a tetramethylsilane internal standard (0 ppm). $^1$H NMR spectra are recorded in the solvent indicated on either a Bruker Avance spectrometer at 500.18 MHz, a Varian Mercury spectrometer at 400.21 MHz, or a GE QE-300 spectrometer at 300.15 MHz. $^{13}$C NMR spectra are recorded in the solvents indicated on the previously mentioned spectrometers at 125.78 MHz, 100.15 MHz, and 75.48 MHz, respectively. IR spectra are recorded on a Nicolet 510P FT-IR spectrometer; electrospray mass spectra are recorded on a Micromass Platform LCZ spectrometer. High resolution mass spectra are recorded on a Micromass QTOF mass spectrometer.

The synthetic process for preparation of a protected disaccharide, compound vi, is outlined in scheme II and exemplified in Example 1, both shown below.

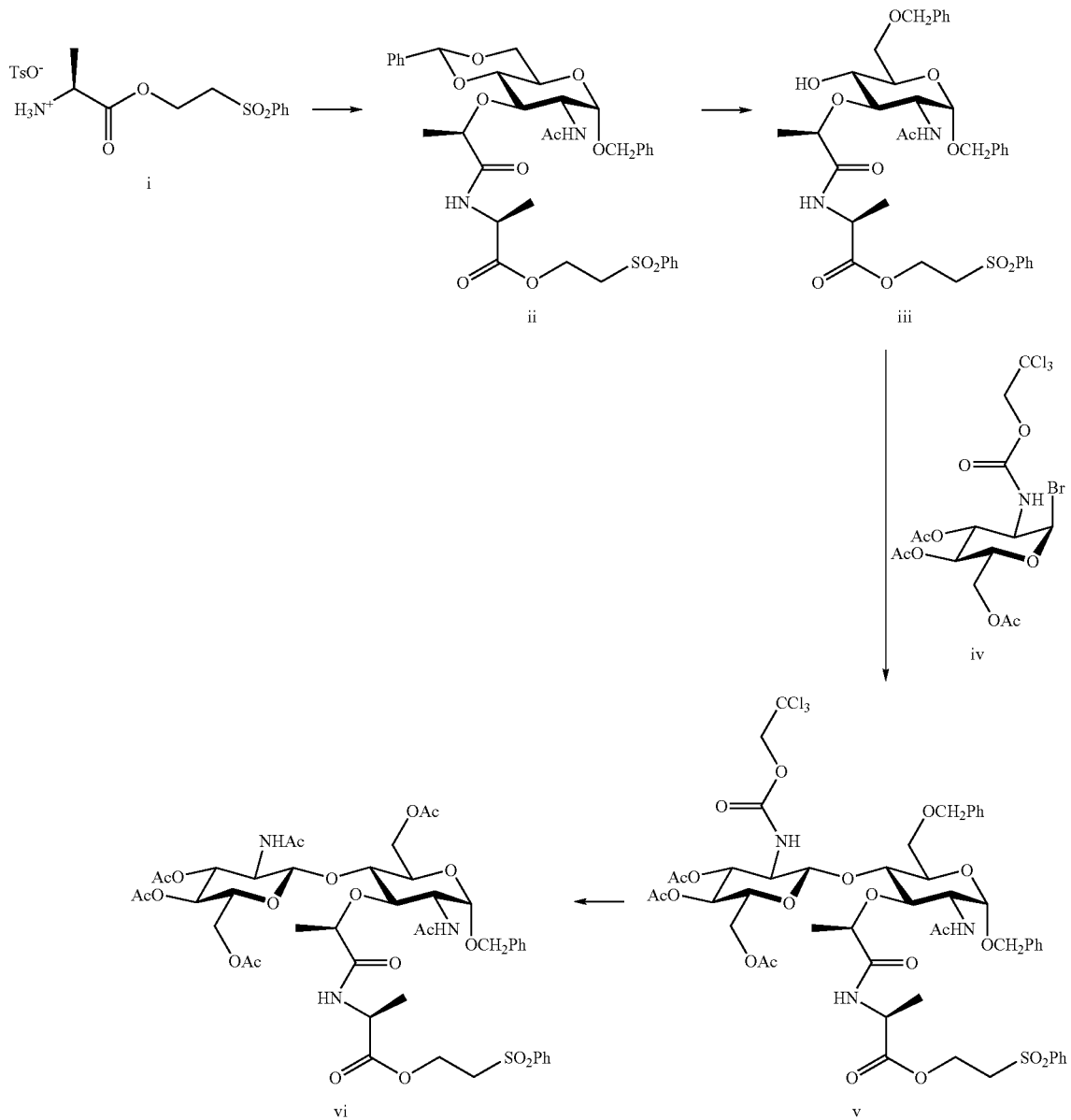

Scheme II

Example 1

I. Regioselective Installation of Benzyl Protection & Attachment of Peptide Linker:

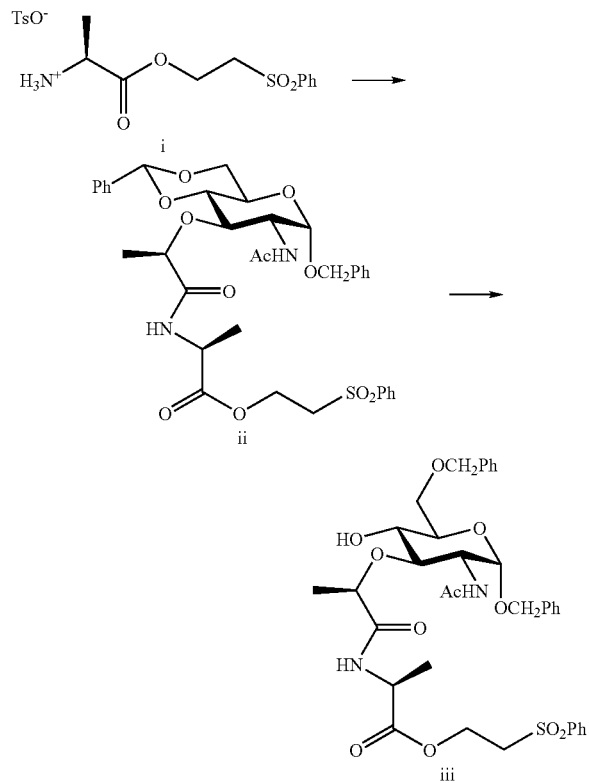

A mixture of (L)-alanine (15.0 g, 168 mmol), phenylsulfonyl ethanol (37.6 g, 202 mmol), and TsOH.H$_2$O (35.2 g, 185 mmol) in benzene (750 mL) is refluxed using a Dean-Stark apparatus. After 16 h, additional phenylsulfonyl ethanol (25 g, 135 mmol) and TsOH.H$_2$O (25 g, 134 mmol) is added along with benzene (180 mL), and the reaction mixture is refluxed overnight. Concentration in vacuo gives the product, compound i, in quantitative yield as a white solid.

Analytical (compound i): $^1$H NMR(DMSO-d$_6$, 300 MHz) δ8.25(br s, impurities, TsOH), 7.94–7.88(m, 2H), 7.81–7.74 (q, J=6.2 Hz, 1H), 7.71–7.62(m, 2H), 7.49(d, J=8.1 Hz, 1H), 7.12(d, J=8.1 Hz, 1H), 5.39(br s, 2H), 4.52–4.44(m, 1H), 4.41–4.33(m, 1H), 3.90–3.82(m, 1H), 3.78(t, J=5.5 Hz, 2H), 3.67(t, J=6.2 Hz, 1H), 3.44(t, J=6.6 Hz, 1H), 2.29(s, 3H +impurities, TsOH), 1.20(d, J=7.3 Hz, 3H) $^{13}$C NMR (DMSO-d$_6$, 75 MHz) δ169.5, 145.5, 139.3, 137.7, 134.1, 133.6, 129.5, 129.3, 128.0, 127.7, 127.6, 125.5, 58.9, 57.5, 54.9, 53.6, 47.7, 20.7, 15.2: MS(ESI) m/z 258.1 (100%, M—TsOH—H); IR KBr) $v_{max}$ 3424(br), 2927(br), 1745(m), 1309(m), 1224(m), 1195(m), 1147(s), 1124(m), 1087(m), 1007(m) cm$^{-1}$; Anal. Calcd for C$_{18}$H$_{25}$NO$_4$S: C, 50.10; H, 5.84; N, 3.25; S, 14.86. Found: C, 48.49; H. 5.31; N, 2.56; S, 14.72.

To a slurry of benzyl N-acetyl-4,6-benzylidine muramic acid (20.0 g, 42.5 mmol) in CH$_2$Cl$_2$ (300 mL) at 0° C. is added N-methylmorpholine (NM) (4.67 mL, 42.5 mmol) and 2-chloro-4,6-dimethoxy-1,3,5-triazine (8.94 g, 51.0 mmol). After stirring for 45 min at 0° C., CH$_2$Cl$_2$ (300 mL) followed by NMM (9.34 mL, 83.0 mmol) and L-alanine (phenylsulfonylethyl ester, tosylate salt) (15.4 g, 51.0 mmol) (i.e., compound i) are added to the above reaction mixture. The resulting solution is slowly warmed to room temperature and stirred for 3 days. The reaction mixture is then filtered. The filtrate is washed first with 1N HCl then with brine, and dried (MgSO$_4$). The filtrate is then concentrated under reduced pressure, evaporated with toluene(×2), and vacuum dried overnight to afford the product, compound ii, (23.5 g, 95%) as a white solid.

Analytical (compound ii): $^1$H MM (CDCl$_3$, 400 MHz) δ7.44(d, J=3.0 Hz, 2H), 7.35(m, 8H), 6.95(d, J=6 Hz, 1H), 6.15(d, J=6.0 Hz, 1H), 5.85(m, 1H), 5.47(s, 1H), 5.21(dd, J=3.0, 12.0 Hz, 1H), 5.30(dd, J=3.0, 15.0 Hz, 1H), 4.90(d, J=3.0 Hz, 1H), 4.72(d, J=12.0 Hz, 1H), 4.60(m, 2H), 4.42(m, 2H), 4.30–4.20(m, 2H), 4.15(q, J=3.0 Hz, 1H), 4.00(q, J=3.0 Hz, 1H), 3.82(m, 1H), 3.75(d, J=9.0 Hz, 1H), 3.65(m, 1H), 1.93(s, 3H), 1.43(d, J=3.0, 9.0 Hz, 3H), 1.38(d, J=3.0, 9.0 Hz, 3H); $^{13}$C NMR (CDCl$_3$, 75 MHz) δ173.2, 172.2, 170.6, 131.6, 129.0, 128.9, 128.4, 128.3, 125.9, 101.4, 97.5, 81.7, 78.3, 76.6, 75.6, 75.1, 70.1, 68.9, 65.8, 64.1, 63.2, 55.3, 53.2, 48.1, 23.0, 17.4, 17.8. MS (PSI) m/z 583.2 (86%, M+H), 581.3(100%, M–H); IR $v_{max}$ (CHCl$_3$) 3010(m), 1740(m), 1681(s), 1616(m), 1569(s), 1523(m), 1470(m), 1377(s), 1333(m), 1119(m), 1090(m) cm$^{-1}$; Anal. Calcd for C$_{31}$H$_{38}$N$_2$O$_9$: C, 63.90; H, 6.57; N, 4.81. Found: C, 63.78; H. 6.55; N, 4.89.

Triethylsilane (16.4 mL, 103 mmol) is added to a solution of compound ii (12.0 g, 20.6 mmol) in CH$_2$Cl$_2$ (150 mL) at 0° C., followed by dropwise addition of TFA (8.1 mL, 103 mmol). The mixture is allowed to stir for 5 h, after which an additional 3 equivalents of TFA (5.0 mL) is added dropwise, and stirred at 0° C. overnight. Upon completion of the reaction, as evidenced by TLC (EtOAc), the reaction mixture is diluted with CH$_2$Cl$_2$, then NaHCO$_3$ is added slowly to neutralize the TFA. The aqueous layer is extracted with CH$_2$Cl$_2$. The organic layer is washed with brine (×2), then dried (MgSO$_4$), and concentrated in vacuo. Purification by prep-LC (eluting with 70:30 EtOAc:hexane to EtOAc), followed by recrystallization from CH$_2$Cl$_2$ and isopropyl ether gives the product, compound iii, (7.4 g, 61%) as a white solid.

Analytical (compound iii): $^1$H NMR (CDCl$_3$, 300 MHz) δ7.38–7.26(m, 10H), 6.99 d, i=7.3 Hz, 1H), 6.16(d, J=8.8 Hz, 1H), 5.94–5.81(m, 1H), 5.30(dd, J=1.1, 17.2 Hz, 1H), 5.22(dd, J=1.1, 10.6 Hz, 1H), 4.92(d, J=3.7 Hz, 2H), 4.68(t, J=11.7 Hz, 1H), 4.59(d, J=7.7 Hz, 4H), 4.49(q, J =6.2 Hz, 1H), 4.46(dd, J=2.2, 11.7 Hz, 2H), 4.21(dq, J=3.7, 9.9 Hz, 1H), 4.17(q, J=7.0 Hz, 1H), 3.83–3.75(m, 1H), 3.71(t, J=5.1 Hz, 1H), 3.68–3.65(m, 1H), 3.54(t, J=10.2 Hz, 1H), 1.89(s, 3H), 1.44(d, J=7.0 Hz, 3H), 1.40(d, J=7.0 Hz, 3H); $^{13}$C NMR(CDCl$_3$, 75 MHz) δ173.0, 172.3, 170.3, 167.7, 137.8, 137.1, 131.7, 128.6, 128.5, 128.1, 127.8, 127.7, 118.5, 97.1, 80.5, 77.7, 73.7, 71.6, 70.5, 70.2, 69.8, 65.8, 55.1, 52.5, 48.0, 24.5, 23.3, 19.2, 17.7; MS(ESI) m/z 585.2 (100%, M+H), 583.2 (100%, M–H); IR $v_{max}$(CHCl$_3$) 3433(m), 3010(m), 1741(m), 1677(s), 1522(m), 1454(m), 1124(m), 1058(m) cm$^{-1}$; Anal. Calcd for C$_3$H$_{40}$N$_2$O$_9$: C, 63.68; H, 6.90; N, 4.79; Found: C, 63.67; H, 6.58; N, 4.83.

II. Glycosidation

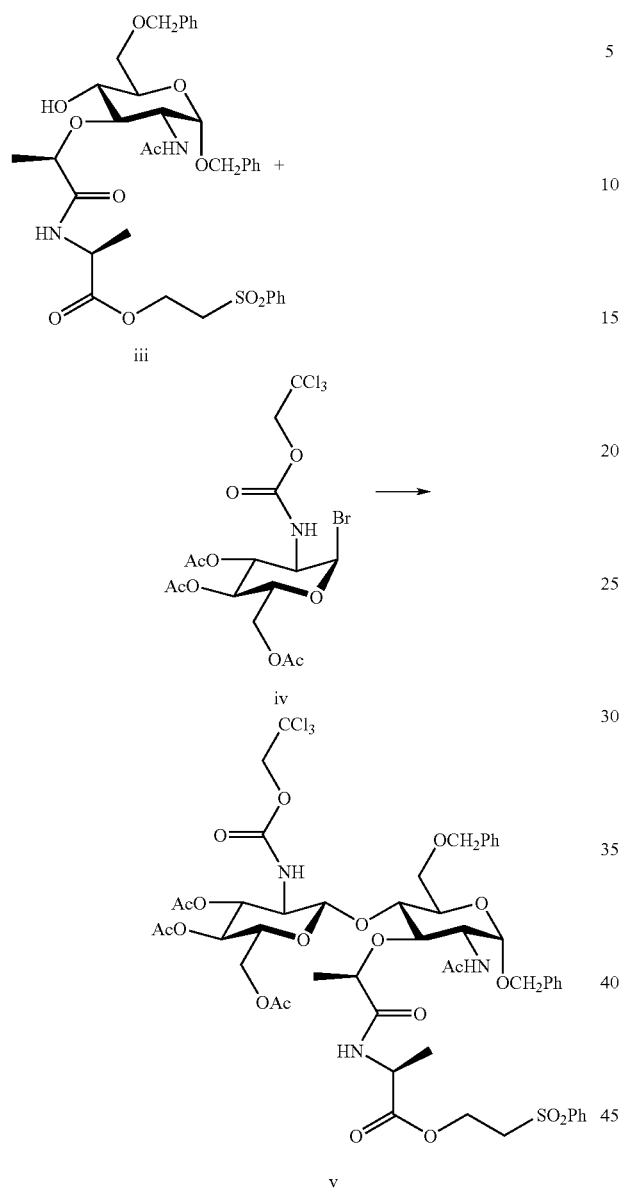

Compound iv is prepared using the procedures described in Imoto, M., *Bull. Chem. Soc. Jpn.*, 60, 2205 (1987).

To a solution of compound iii (4.59 g, 6.43 mmol) in CH$_2$Cl$_2$ (30 mL) are added 4Å molecular sieves (10 g) and silver triflate (5.12 g, 20.0 mmol). To this mixture is added a solution of freshly prepared compound iv (10.8 g, 20.0 mmol) in CH$_2$Cl$_2$ (9.5 mL) in four portions over a 1 h period. Each of the starting materials is dried prior to use, and the reaction is performed under controlled anhydrous conditions. After stirring at room temperature for 24 h, the reaction mixture is filtered through Celite and washed with CH$_2$Cl$_2$. The organic layer is washed with NaHCO$_3$, brine, dried (Na$_2$SO$_4$), and concentrated in vacuo. Purification by column chromatography on silica (Flash Elute system) utilizing a solvent gradient of 50% hexane in EtOAc, 15% hexane in EtOAc, EtOAc, and 5% MeOH in EtOAc yields the product, compound v, (5.73 g, 76%) as a white solid, along with unreacted starting material, compound iii, (630 mg, 14%).

Analytical (compound v): $^1$H NMR(CDCl$_3$, 300 MHz) δ7.91(d, J=7.0 Hz, 2H), 7.66(t, J=7.3 Hz, 1H), 7.58–7.50(m, 4H), 7.45(t, J=7.3 Hz, 2H), 7.33–7.26(m, 6H), 6.83(d, J=7.3 Hz, 1H), 6.52(d, J=7.0 Hz, 1H), 5.09(d, J =2.9 Hz, 1H), 4.97(t, J=9.5 Hz, 1H), 4.87(d, J=12.1 Hz, 1H), 4.79–4.73(m, 2H), 4.60(dd, J=7.3, 12.1 Hz, 2H), 4.53–4.29(m, 5H), 4.26–4.04(m, 7H), 4.00–3.88(m, 2H), 3.70–3.50(m, 4H), 3.42(t, J=10.6 Hz, 4H), 2.03(s, 3H), 1.98(s, 6H), 1.89(s, 3H), 1.34(d, J=6.6 Hz, 3H), 1.24(d, J=7.3 Hz, 3H); $^{13}$C NMR (CDCl$_3$, 75 MHz) δ173.4, 171.8, 170.6, 170.3, 169.4, 154.1, 137.3, 134.0, 129.4, 129.1, 128.5, 128.1, 100.0, 97.1, 96.9, 77.4, 77.0, 76.6, 75.7, 74.5, 73.8, 72.2, 71.2, 70.4, 70.3, 68.3, 67.2, 61.5, 58.1, 26.2, 54.9, 53.6, 47.7, 23.2, 20.6, 18.3, 17.5; MS (FAB) m/z 1176.3 (73%, M+H), (ESI) m/z 1174.5 (62%, M−H) IR (KBr) ν$_{max}$ 3385(br), 3067(w), 2939(w), 1753(s), 1669 m), 1537(m), 1233(s), 1145(m), 1045(s) cm$^{-1}$; UV-vis (95% EtOH) λ$_{max}$ 264 (1223.11)nm; Anal. Calcd for C$_{51}$H$_{64}$Cl$_3$N$_3$O$_{20}$S: C, 52.02; H, 5.48; N, 3.57; S, 2.72; Cl, 9.03. Found: C, 51.72; H, 5.40; N, 3.64; S, 2.72; Cl, 9.07.

III. Protective Group Interchange

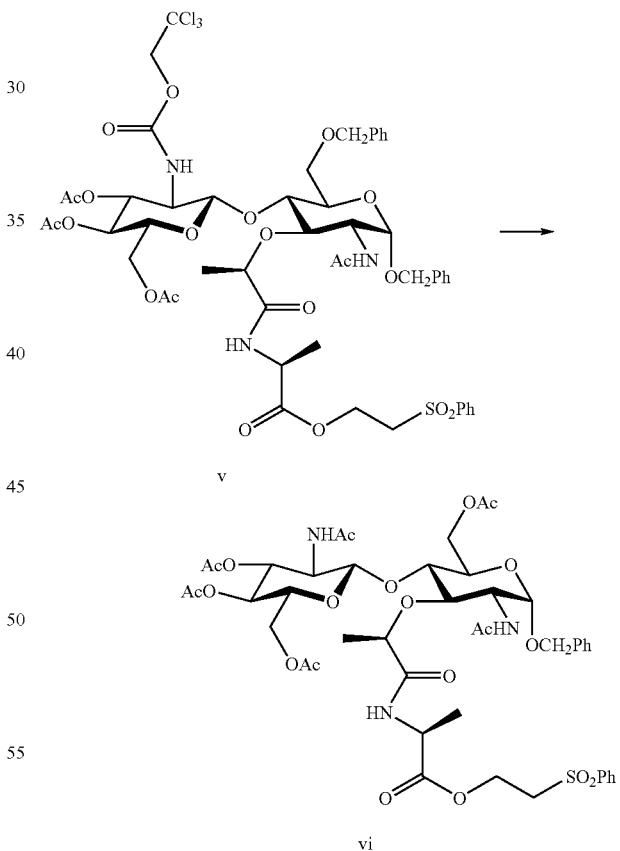

To a solution of compound v (1.9 g, 1.57 mmol) in Ac$_2$O:AcOH (2:1, 11 mL) is added a solution of ZnCl$_2$ (2.1 g, 15.7 mmol) in Ac$_2$O:ACOH (2:1, 5 mL) in one portion. Upon completion of the reaction (24 h) as judged by TLC (EtOAc), Troc is removed by adding Zn dust (4.1 g, 62.8 mmol) and a mixture of THF:Ac$_2$O:AcOH (3:2:1, 25 mL) to the above reaction mixture and stirring until no starting material is evidenced by TLC (EtOAc). The reaction mixture is filtered through Celite, washed with EtOAc, and then concentrated under reduced pressure. The residue is repeatedly evaporated with toluene to remove any remaining $Ac_2O$ and AcOH, and then diluted with EtOAc. The organic layer is washed with $NaHCO_3$ (×2), $H_2O$ (×2), and brine. The organic layer is then dried ($Na_2SO_4$) and concentrated in vacuo. Purification via column chromatography on silica (Flash Elute system) eluting with 2% MeOH in EtOAc affords the product, compound vi, (1.0 g, 67%) as a white solid.

Analytical (compound vi): $^1H$ NMR ($CDCl_3$, 300 MHz) δ7.89(d, J=7.0 Hz, 2H), 7.66(t, J=7.3 Hz, 1H), 7.56(t, J=7.7 Hz, 2H), 7.34–7.23(m, 6H), 7.16(d, J=7.7 Hz, 1H), 6.88(d, J=7.0 Hz, 1H), 6.12(d, J=9.5 Hz, 1H), 5.12–5.07(m, 3H), 4.56 (dd, J=12.1, 40.0 Hz, 2H), 4.45(d, J=9.0 Hz, 1H), 4.39(d, J=8.4 Hz, 1H), 4.35–4.23(m, 4H), 4.17(d, J=12.0 Hz, 2H), 4.09–3.95(m, 3H), 3.78(d, J=5.5 Hz, 2H), 3.60–3.48(m, 3H), 3.41–3.30(m, 2H), 2.12(s, 3H), 2.01(s, 3H), 2.00(s, 3H), 1.99(s, 3H), 1.94(s, 3H), 1.92(s, 3H), 1.38 (d, J=6.6 Hz, 3H), 1.28(d, J=7.3 Hz, 3H); $^{13}C$ NMR($CDCl_3$, 75 MHz) δ173.8, 171.9, 171.2, 170.9, 170.8, 170.6, 169.3, 139.2, 137.3, 134.1, 129.4, 128.9, 128.5, 128.1, 128.0, 127.8, 100.2, 96.9, 77.1, 76.6, 75.9, 75.6, 72.5, 71.8, 70.2, 69.5, 68.2, 62.3, 61.6, 58.0, 54.9, 54.6, 53.6, 47.8, 23.2, 23.1, 20.9, 20.6, 18.4, 17.3; MS (ESI) m/z 994.7 (100%, M–H); IR (KBr) $v_{max}$ 3384(br), 3301(br), 3068(w), 2939(w), 1748(s), 1670(s), 1540(m), 1372(m), 1236(s), 1144(m), 1041(s) $cm^{-1}$; Anal. Calcd for $C_{45}H_{61}N_3O_{20}S$: C, 54.26; H, 6.17; N, 4.22; S, 3.22. Found: C, 53.96; H, 5.78; N, 4.17; S, 3.09.

Scheme III and Example III, both shown below, illustrate the synthesis of GMDP from compound vi.

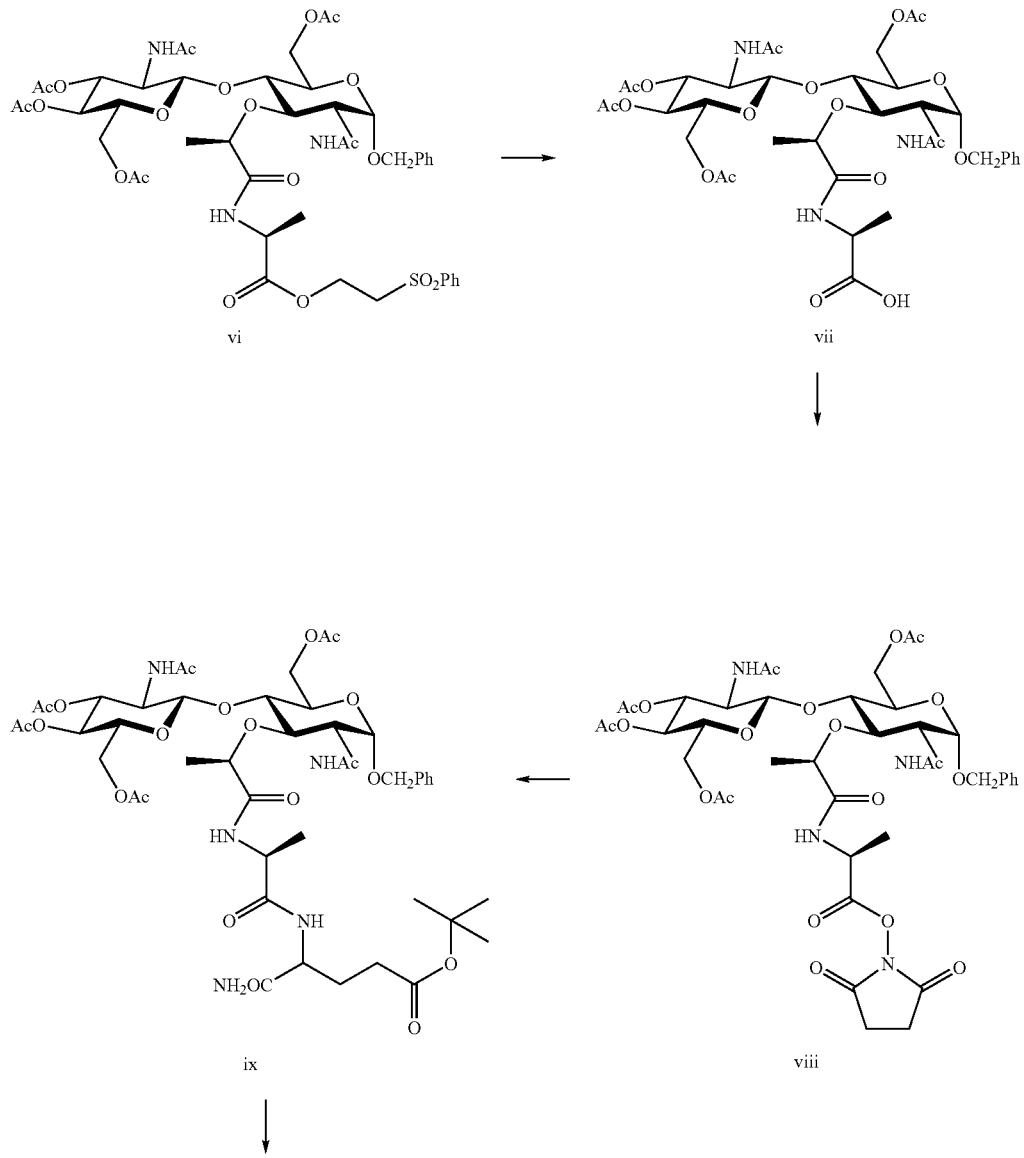

Scheme III

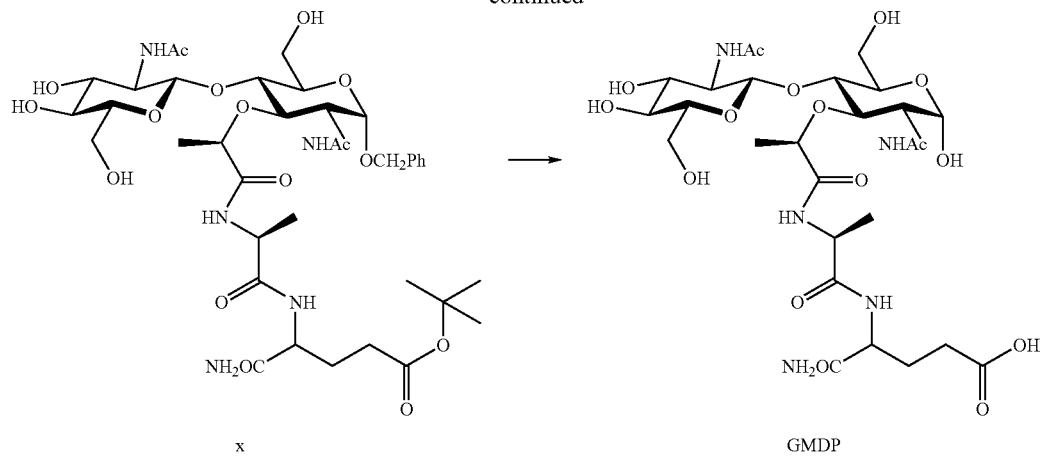

x

GMDP

Example 2

I. Preparation of Compound vii

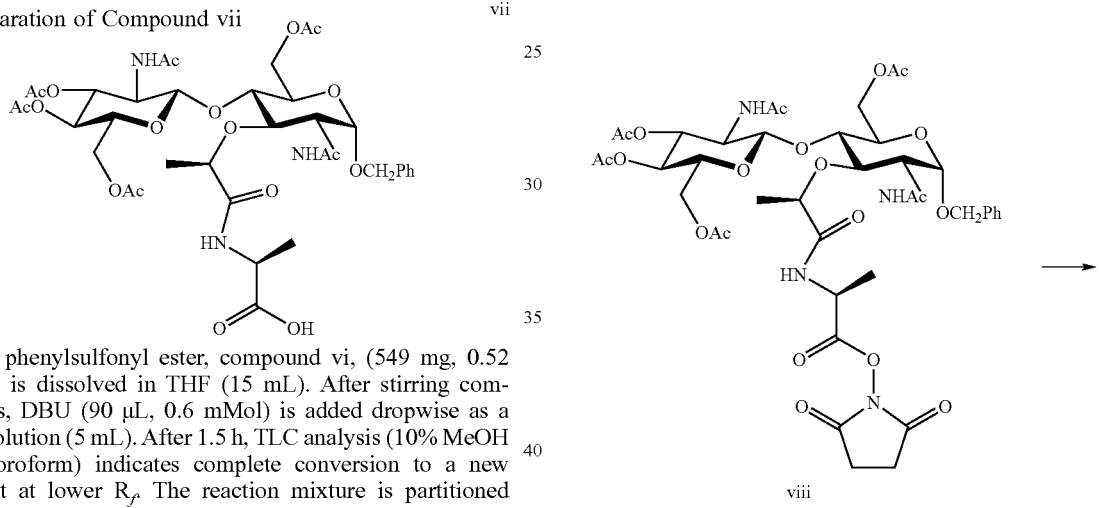

The phenylsulfonyl ester, compound vi, (549 mg, 0.52 mMol) is dissolved in THF (15 mL). After stirring commences, DBU (90 μL, 0.6 mMol) is added dropwise as a THF solution (5 mL). After 1.5 h, TLC analysis (10% MeOH in chloroform) indicates complete conversion to a new product at lower $R_f$. The reaction mixture is partitioned between EtOAc and 1 N HCl. The organic phase is layered with water and, with vigorous stirring, the pH is adjusted to 8.8 with 2 N NaOH (meter). In a similar manner, the basic aqueous phase is layered with chloroform, the system is stirred vigorously while the pH is adjusted to 1.5 with concentrated HCl. The acidic aqueous phase is extracted again with chloroform. The combined chloroform solutions are dried (MgSO$_4$) and concentrated to give the desired disaccharide acid, compound vii, as a colorless solid (412 mg, 96%). ESI-MS (negative ion)=824.8.

II. Preparation of Compound ix

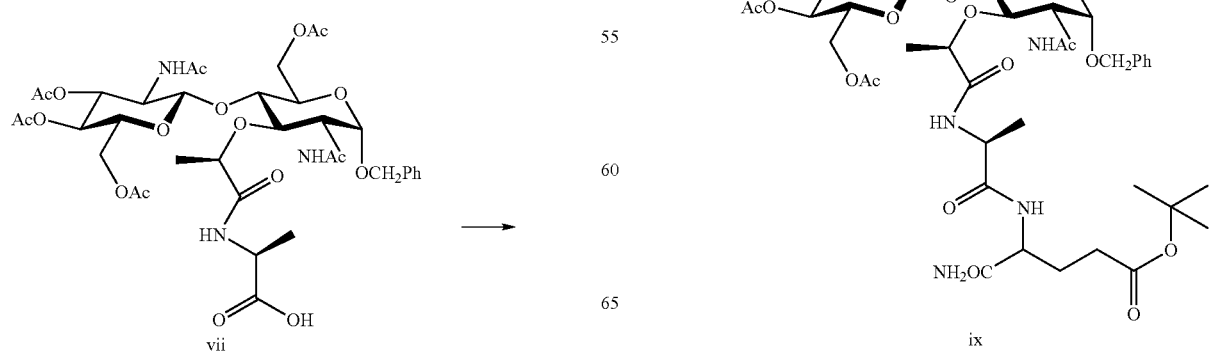

The disaccharide acid, compound vii, (1.02 g, 1.24 mMol) is slurried in acetonitrile. N-hydroxysuccinimide (156 mg, 1.36 mMol) and EDCI (261 mg, 1.36 mMol) are then added. The system becomes homogeneous immediately. After 4 h, TLC analysis (10% MeOH in chloroform) indicates complete formation of the NHS active ester intermediate, i.e., compound viii. A solution of γ-Obu$^t$-iso-Gln (275 mg, 1.36 mMol) in 2:1=acetonitirile:DMF (5 mL) is added dropwise, followed immediately by diisopropylethyl amine (237 μL, 1.36 mMol). After 3.5 h, TLC analysis (10% MeOH in chloroform) indicates complete conversion of the active ester to the desired glycodipeptide at $R_f$=0.32. A small amount of a very slightly higher $R_f$ product, possibly the diastereomer at Ala, is also observed. The reaction mixture is partitioned between EtOAc and N HCl. The organic phase is dried (MgSO4) and concentrated to a solid. The crude product is adsorbed on silica gel (10 g), and chromatographed over silica gel (10 g) using an elution gradient of chloroform to 10% MeOH in chloroform. The product thus obtained, tetraacetyl glycodipeptide (compound ix), (colorless solid, 1.10 g, 88%) is diastereomerically pure. ESI-MS (positive ion)=1010.4, 1032.4

III. Preparation of GMPD

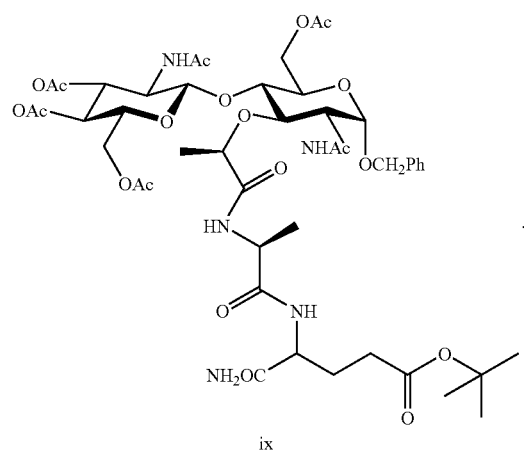

ix

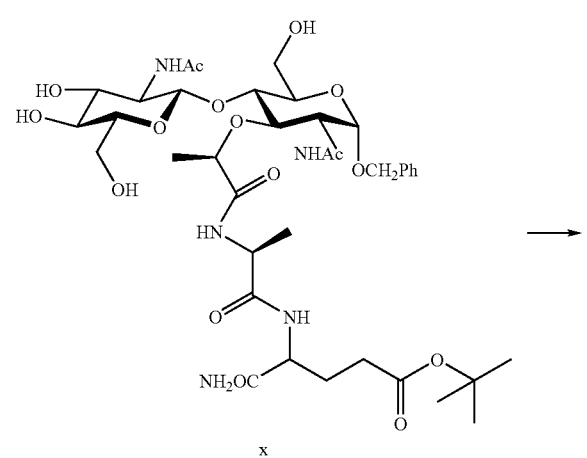

x

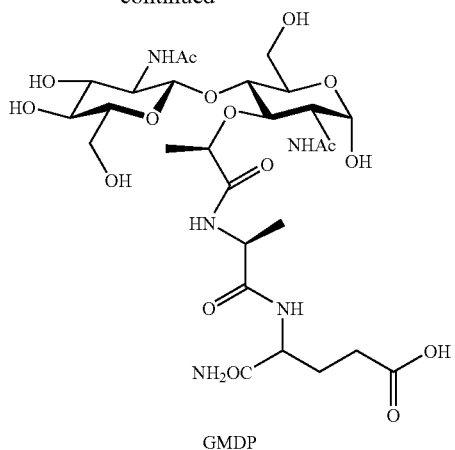

GMDP

The tetraacetyl glycodipeptide (compound ix) (1.02 g, 1.0 mMol) is dissolved in dry MeOH (25 mL). A solution of 0.5 M NaOMe in MeOH (2.0 mL, 1 mMol) is added with stirring.

The reaction mixture is stirred at room temperature until ESI-MS analysis indicates that all four acetyl groups have been removed, thereby forming the tetrahydroxy plycopeptide (compound x) (positive ion, M+H=843). Dowex resin 50WX8-400 is added portionwise with stirring until the apparent pH (paper) reaches 4–5. The resin is removed by filtration and the solution concentrated to a thick oil. The oil is taken up in 0.25 M HCl in ethanol and stirred at room temperature for 3 hr. Pd/C (0.5 g) is added to the reaction mixture, and the system is brought under a hydrogen atmosphere. After 2.5 h, the catalyst is removed by filtration and the filtrate concentrated in vacuo. The concentrate is lyophilized twice from saturated aqueous $NH_4HCO_3$ to afford GMDP as an off-white solid (598 mg, 86%). ESI-MS (positive ion, M+14=709.4; negative ion, M−H=693.9).

What is claimed is:

1. A process for preparing a protected glycopeptide of formula 1

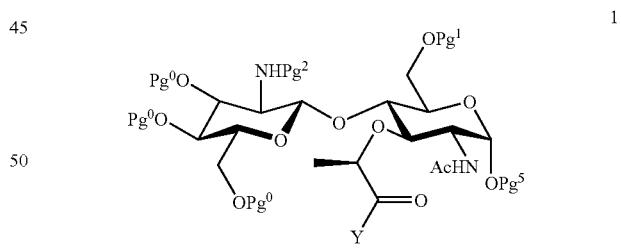

comprising: coupling a muramylamide compound of formula 2

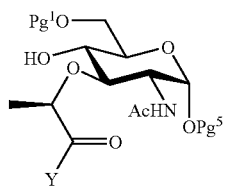

with a glucopyranosyl compound of formula 3

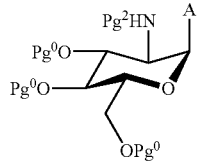

3 to form said glycopeptide of formula 1, wherein:
A is Br or Cl;
$Pg^0$ is an acyl hydroxy-protecting group;
$Pg^1$ is a hydroxy-protecting group which is not electron withdrawing;
$Pg^2$ is an amine-protecting group which does not lead to oxazoline formation;
$Pg^5$ is a hydroxy-protecting group;
$Pg^0$, $Pg^1$, $Pg^2$ and $Pg^5$ are orthogonal protecting groups; and
Y is a residue of an amino acid or peptide of 2 to 5 amino acid residues, wherein:
Y forms an amide linkage with the attached carbonyl; and
Y comprises a protected terminal carboxy group.

2. The process of claim 1, wherein said reacting is carried out under extreme anhydrous conditions.

3. The process of claim 1, wherein $Pg^1$ is benzyl.

4. The process of claim 3, wherein said muramylamide of formula 2 is prepared by reductively opening the 1,3-dioxane ring of a compound of formula 6

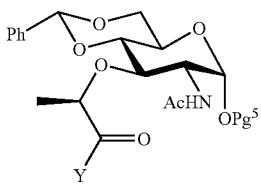

6 wherein:
$Pg^5$ is a hydroxy-protecting group which does not lead to oxazoline formation; and
Y is a residue of an amino acid or peptide of 2 to 5 amino acid residues, wherein:
Y forms an amide linkage with the attached carbonyl; and
Y comprises a protected terminal carboxy group.

5. The process of claim 1, further comprising: exchanging said $Pg^1$ group of said compound of formula 1 with a $Pg^3$ group to form a compound of formula 10

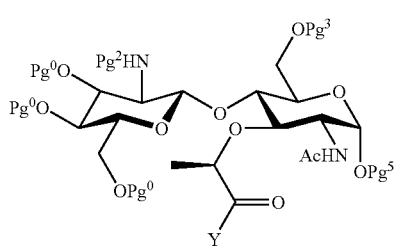

10 wherein:
$Pg^0$ is an acyl hydroxy-protecting group;
$Pg^2$ is an amine-protecting group which does not lead to oxazoline formation;
$Pg^3$ is acyl hydroxy-protecting group;
$Pg^5$ is a hydroxy-protecting group;
$Pg^3$, $Pg^2$, and $P^5$ are mutually orthogonal protecting groups; and
Y is a residue of an amino acid or peptide of 2 to 5 amino acid residues, wherein:
Y forms an amide linkage with the attached carbonyl; and
Y comprises a protected terminal carboxy group.

6. The process of claim 5, wherein $Pg^1$ is benzyl.

7. The process of claim 5, wherein $Pg^3$ is acetyl.

8. The process of claim 5, further comprising: exchanging said $Pg^2$ group of said compound of formula 10 acetyl group to form a compound of formula 9

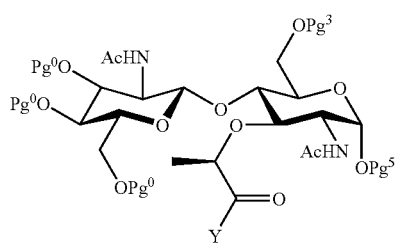

9 wherein:
$Pg^0$ is an acyl hydroxy-protecting group;
$Pg^3$ is an acyl hydroxy-protecting group;
$Pg^5$ is a hydroxy-protecting group;
$Pg^0$ and $Pg^3$ are orthogonal to $Pg^5$; and
Y is a residue of an amino acid or peptide of 2 to 5 amino acid residues, wherein:
Y forms an amide linkage with the attached carbonyl; and
Y comprises a protected terminal carboxy group.

9. The process of claim 8, wherein $Pg^2$ is 2,2,2-trichloroethoxycarbonyl.

10. The process of claim 9, wherein $Pg^1$ is benzyl and $Pg^3$ is acetyl.

11. The process of claim 10, wherein said exchanging of said $Pg^1$ and $Pg^2$ groups comprises:
(a) dissolving said compound of formula 1 in acetic anhydride and acetic acid;
(b) adding anhydrous zinc chloride to exchange said $Pg^1$ group with an acetyl group; and
(c) adding zinc dust to exchange said $Pg^2$ group with said acetyl group.

12. The process of claim 8, further comprising: deprotecting said terminal carboxy group of said Y group of said compound of formula 9 to form a compound of formula 8

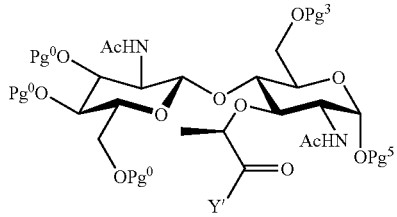

wherein:
- $Pg^0$ is an acyl hydroxy-protecting group;
- $Pg^3$ is an acyl hydroxy-protecting group;
- $Pg^5$ is a hydroxy-protecting group;
- $Pg^0$ and $Pg^3$ are orthogonal to $Pg^5$; and
- Y' is a residue of an amino acid or peptide of 2 to 5 amino acid residues wherein Y forms an amide linkage with the attached carbonyl.

13. The process of claim 12, further comprising: saponifying said $Pg^0$ and $Pg^3$ groups of said compound of formula 9 to form a compound of formula 7

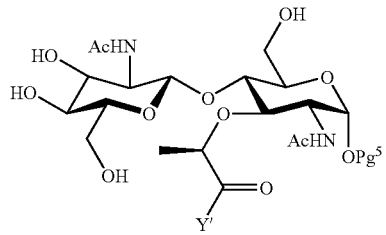

wherein:
- $Pg^5$ is a hydroxy-protecting group; and
- Y' is a residue of an amino acid or peptide of 2 to 5 amino acid residues, where Y' forms an amide linkage with the attached carbonyl.

14. The process of claim 13, further comprising: removing said $Pg^5$ group of said compound of formula 7 to form a compound of formula I

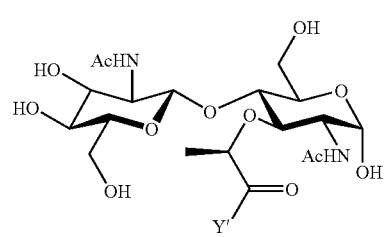

wherein:
- Y' is a residue of an amino acid or peptide of 2 to 5 amino acid residues; and
- Y' forms an amide linkage with the attached carbonyl.

15. The process of claim 14, wherein $Pg^5$ is benzyl.

16. The process of claim 1, wherein said glycopeptide is of formula 1a

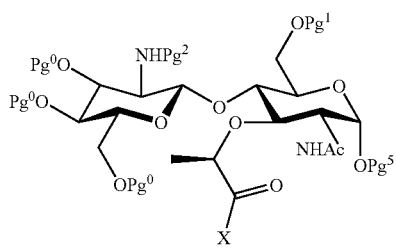

wherein:
- $Pg^0$ is an acyl hydroxy-protecting group;
- $Pg^1$ is a hydroxy-protecting group which is not electron withdrawing;
- $Pg^2$ is an amine-protecting group which does not lead to oxazoline formation;
- $Pg^5$ is a hydroxy-protecting group;
- $Pg^0$, $Pg^1$, $Pg^2$, and $Pg^5$ are mutually orthogonal protecting groups; and
- X is a residue of an amino acid or peptide of 2 to 4 amino acid residues, wherein:
  - X forms an amide linkage with the attached carbonyl; and
  - X comprises a protected terminal carboxy group.

17. The process of claim 16, further comprising: exchanging said $Pg^1$ group of said compound of formula 1a with a $Pg^3$ group to form a compound of formula 19

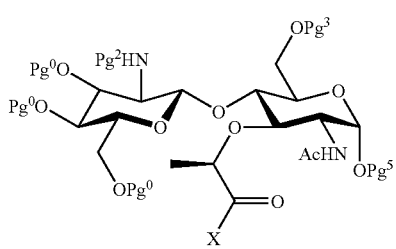

wherein:
- $Pg^0$ is an acyl hydroxy-protecting group;
- $Pg^2$ is an amine-protecting group which does not lead to oxazoline formation;
- $Pg^3$ is an acyl hydroxy-protecting group;
- $Pg^5$ is a hydroxy-protecting group;
- $Pg^3$, $Pg^2$ and $Pg^5$ are mutually orthogonal protecting groups; and
- X is a residue of an amino acid or peptide of 2 to 4 amino acid residues, wherein:
  - X forms an amide linkage with the attached carbonyl; and
  - X comprises a protected terminal carboxy group.

18. The process of claim 17, wherein $Pg^1$ is benzyl.

19. The process of claim 17, wherein $Pg^3$ is acetyl.

20. The process of claim 17, further comprising: exchanging said Pg² group of said compound of formula 19 with an acetyl group to form a compound of formula 18

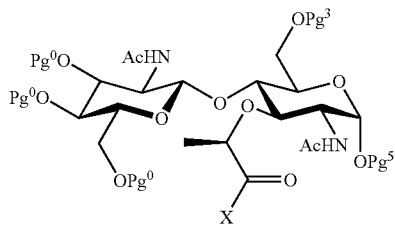

18 wherein:
Pg⁰ is an acyl hydroxy-protecting group;
Pg³ is an acyl hydroxy-protecting group;
Pg⁵ is a hydroxy-protecting group;
Pg⁰ and Pg³ are orthogonal to Pg⁵; and
X is a residue of an amino acid or peptide of 2 to 4 amino acid residues, wherein:
    X forms an amide linkage with the attached carbonyl; and
    X comprises a protected terminal carboxy group.

21. The process of claim 20, wherein Pg² is 2,2,2-trichloroethoxycarbonyl.

22. The process of claim 21, wherein Pg¹ is benzyl and Pg³ is acetyl.

23. The process of claim 22, wherein said exchanging of said Pg¹ and Pg² groups comprises:
(a) dissolving said compound of formula 1a in acetic anhydride and acetic acid;
(b) adding anhydrous zinc chloride to exchange said Pg¹ group with an acetyl group; and
(c) adding zinc dust to exchange said Pg² group with said acetyl group.

24. The process of claim 20 further comprising: deprotecting said terminal carhoxy group of X group of said compound of formula 18 to form a compound of formula 17

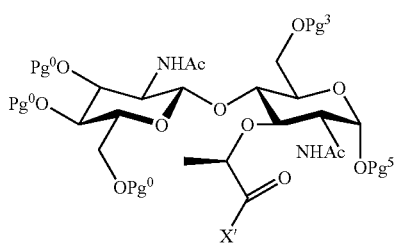

17 wherein:
Pg⁰ is an acyl hydroxy-protecting group;
Pg³ in an acyl hydroxy-protecting group;
Pg⁵ is a hydroxy-protecting group;
Pg⁰ and Pg³ are orthogonal to Pg⁵; and
X' is a residue of an amino acid or peptide of 2 to 4 amino acid residues, where X' forms an amide linkage with the attached carbonyl.

25. The process of claim 24, further comprising: reacting said compound of formula 17 with a compound of formula LOH to form an activated ester of formula 15

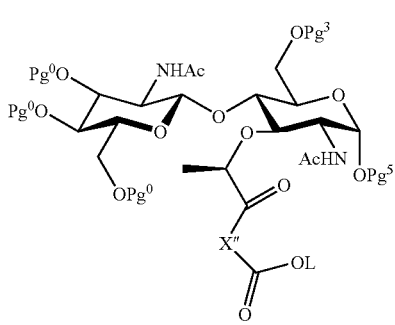

15 wherein:
Pg⁰ is an acyl hydroxy-protecting group;
Pg³ is an acyl hydroxy-protecting group;
Pg⁵ is a hydroxy-protecting group;
Pg⁰ and Pg³ are orthogonal to Pg⁵;
X'''C(O)OL is the activated ester of X';
—OL is a leaving group susceptible to displacement by an amine nucleophile; and
X' is a residue of an amino acid or peptide of 2 to 4 amino acid residues, where X' forms an amide linkage with the attached carbonyl.

26. The process of claim 25, wherein LOH is N-hydroxysuccinimide.

27. The process of claim 25, further comprising: coupling said compound of formula 15 with a compound of formula WH to form a compound of formula 13

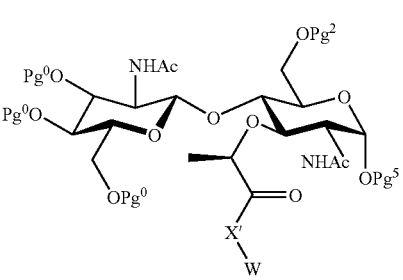

13 wherein:
Pg⁰ is an acyl hydroxy-protecting group;
Pg³ is an acyl hydroxy-protecting group;
Pg⁵ is a hydroxy-protecting;
Pg⁰ and Pg³ are ortogonsi to Pg⁵;
X' is a residue of an amino acid or peptide, where X' forms an amide linkage with the attached carbonyl;
W is a residue of an amino acid or peptide, where W comprises a protected terminal carboxy group;
and W and X' together consist of 2 to 5 amino acid residues.

28. The process of claim 27, further comprising: saponifying said $Pg^0$ and $Pg^3$ groups of said compound of formula 13 to form a compound of formula 12

[Structure 12]

wherein:
  $Pg^5$ is a hydroxy-protecting;
  X' is a residue of an amino acid or peptide, where X' forms an amide linkage with the attached carbonyl;
  W is a residue of an amino acid or peptide, where W comprises a protected terminal carboxy group;
  and X' and W together consist of 2 to 5 amino avid residues.

29. The process of claim 28, wherein $Pg^0$ is acetyl.

30. The process of claim 28, wherein $Pg^3$ is acetyl.

31. The process of claim 28, further comprising: removing said $Pg^5$ group of said compound of formula 12 to form a compound of formula 11

[Structure 11]

wherein:
  X' is a residue of an amino acid or peptide, where X' forms an amide linkage with the attached carboxyl;
  W is a residue of an amino acid or peptide, where W comprises a protected terminal carboxy group;
  and X' and W together consist of 2 to 5 amino acid residues.

32. The process of claim 31, wherein $Pg^5$ is benzyl.

33. The process of claim 31, further comprising: deprotecting said W group of said compound of formula 11 to form a compound of fonnula I

[Structure I]

wherein:
  —Y' is —X'—W';
  X' is a residue of an amino acid or peptide, where X' forms an amide linkage with the attached carbonyl;
  W' is a residue of an amino acid or peptide
  and X' and W' together consist of 2 to 5 amino acid residues.

34. The process of claim 1, wherein A is Br.

35. The process of claim 1, wherein $Pg^2$ is a carbamate or imide amine-protecting group.

36. The process of claim 35, wherein $Pg^2$ is a carbamate or imide amine-protecting group.

37. The process of claim 36, wherein $Pg^2$ is 2,2,2-trichloroethoxycarbonyl.

38. The process of claim 1, wherein $Pg^1$ is a benzyl, allyl or silyl hydroxy-protecting group.

39. The process of claim 38, wherein $Pg^1$ is benzyl.

40. The process of claim 1, wherein $Pg^0$ is acetyl.

41. The process of claim 1, wherein $Pg^5$ is a benzyl, allyl or n-pentenyl hydroxy-protecting group.

42. The process of claim 41, wherein $Pg^5$ is benzyl.

43. The process of claim 1, wherein Y is a linear peptide.

44. The process of claim 16, wherein X is a linear peptide.

45. The process of claim 27, wherein:
  X' is a peptide of 2–4 amino acid residues; and
  W is a peptide of 2–4 amino acid residues, provided that X' and W together consist of 2 to 5 amino acid residues.

46. The process of claim 27, wherein —X'—W is a linear peptide.

* * * * *